(12) United States Patent
Hausknecht

(10) Patent No.: US 8,173,626 B2
(45) Date of Patent: May 8, 2012

(54) METHODS, DOSING REGIMENS AND MEDICATIONS USING ANTI-PROGESTATIONAL AGENTS FOR THE TREATMENT OF DISORDERS

(75) Inventor: Richard Hausknecht, Bronx, NY (US)

(73) Assignee: Danco Laboratories LLC, New York, NY (US)

( * ) Notice: Subject to any disclaimer, the term of this patent is extended or adjusted under 35 U.S.C. 154(b) by 1328 days.

(21) Appl. No.: 11/715,509

(22) Filed: Mar. 8, 2007

(65) Prior Publication Data

US 2007/0213306 A1 Sep. 13, 2007

Related U.S. Application Data

(60) Provisional application No. 60/780,047, filed on Mar. 8, 2006.

(51) Int. Cl.
*A61K 31/56* (2006.01)
(52) U.S. Cl. .................................................. 514/179
(58) Field of Classification Search .................. 514/179
See application file for complete search history.

(56) References Cited

U.S. PATENT DOCUMENTS

| | | |
|---|---|---|
| 5,468,741 A | 11/1995 | Yen |
| 6,043,234 A | 3/2000 | Stockemann et al. |
| 6,451,780 B1 | 9/2002 | Chwalsz et al. |

OTHER PUBLICATIONS

Lumsden and Wallace, Bailliere's Clinical Obstetrics and Gynaecology, 1998;12(2):177-195.*
Eldar-Geva, Bailliere's Clinical Obstetrics and Gynaecology, 1998;12(2):269-288.*
Chwalisz et al., Presentation at Advances in Leiomyoma Research 2nd NIH International Congress, Feb. 2005, Bethesda, MD.*
Chu et al., Successful Long-Term Treatment of Refractory Cushings Disease with High-Dose Mifepristone (RU 486). J. Clin. Endocrinol. Metab. Aug. 2001, vol. 86, No. 8, pp. 3568-3573.
Eisinger et al., Low-Dose Mifepristone for Uterine Lelomyomata. J. Obstet. Gynecol., Feb. 2003, vol. 101, No. 2, pp. 243-250.
Xu et al., The Journal of Clinical Endocrinology & Metabolism 90(2):953-961 (2005).
NIH Record, 57(24):1-12, Dec. 2, 2005.

* cited by examiner

*Primary Examiner* — San-Ming Hui
(74) *Attorney, Agent, or Firm* — Don J. Pelto, Esquire; Sheppard, Mullin, Richter & Hampton LLP

(57) ABSTRACT

The present invention relates to the treatment of disorders using anti-progestational agents. More specifically, the present invention relates to the treatment of disorders using low doses of anti-progestational agents. Compared to dosages and lengths of treatment taught by the prior art, the described methods, dosing regimens and medications use effective dosages and lengths of treatment that are lower and/or shorter than previously thought possible.

47 Claims, 5 Drawing Sheets

| | Treatment (n=22) | | | Placebo (n=20) | | |
|---|---|---|---|---|---|---|
| | Mean (SD) | Median | Range | Mean (SD) | Median | Range |
| Age (y) | 44.8 (6.2) | 43 | 29-54 | 43.2 (4.7) | 44 | 31-50 |
| Body mass index (kg/m²) | 31.7 (8.7) | 32 | 21-52 | 27.2 (5.6) | 26 | 20-39 |
| Education (y) | 14.6 (2.3) | 14 | 12-19 | 15.1 (2.5) | 15 | 11-22 |
| Gravidity | 2.6 (2.1) | 3 | 0-7 | 2.4 (2.1) | 2 | 0-7 |
| Parity | 1.8 (1.6) | 2 | 0-6 | 1.6 (1.5) | 2 | 0-5 |
| Uterine volume (mL) | 719 (663) | 506 | 173-2,488 | 449 (236) | 392 | 210-1,103 |
| African American [n (%)] | 11 (50) | – | – | 11 (55) | – | – |

SD, standard deviation.

Figure 1

|  | Treatment (n=22) | | | Placebo (n=20) | | |
| --- | --- | --- | --- | --- | --- | --- |
|  | Mean (SD) | Median | Range | Mean (SD) | Median | Range |
| Age (y) | 44.8 (6.2) | 43 | 29-54 | 43.2 (4.7) | 44 | 31-50 |
| Body mass index (kg/m$^2$) | 31.7 (8.7) | 32 | 21-52 | 27.2 (5.6) | 26 | 20-39 |
| Education (y) | 14.6 (2.3) | 14 | 12-19 | 15.1 (2.5) | 15 | 11-22 |
| Gravidity | 2.6 (2.1) | 3 | 0-7 | 2.4 (2.1) | 2 | 0-7 |
| Parity | 1.8 (1.6) | 2 | 0-6 | 1.6 (1.5) | 2 | 0-5 |
| Uterine volume (mL) | 719 (663) | 506 | 173-2,488 | 449 (236) | 392 | 210-1,103 |
| African American [n (%)] | 11 (50) | – | – | 11 (55) | – | – |

SD, standard deviation.

METHODS, DOSING REGIMENS AND MEDICATIONS USING ANTI-PROGESTATIONAL AGENTS FOR THE TREATMENT OF DISORDERS

CROSS REFERENCE TO RELATED APPLICATION

This application claims the benefit, under 35 U.S.C. §119, of provisional U.S. Application Ser. No. 60/780,047, filed Mar. 8, 2006, the entire contents and substance of which is hereby incorporated by reference.

FIELD OF THE INVENTION

The present invention relates to the treatment of disorders using anti-progestational agents. More specifically, the present invention relates to the treatment of disorders using low doses of anti-progestational agents. The disorders treated can be, but are not limited to, benign gynecological disorders.

BACKGROUND OF THE INVENTION

Progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of medical conditions.

Information indicating that anti-progestational agents could be effective in a number of medical conditions is available. For example, this information has been summarized in a report from the Institute of Medicine compiled by Donaldson et al., Editors, Clinical Applications of Mifepristone (RU 486) and Other Anti-progestational agents, Committee on Anti-progestational agents: Assessing the Science, Institute of Medicine, National Academy Press, (1993). The following discussion regarding uterine leiomyomata highlights one non-limiting example of such uses.

Uterine leiomyomata (also called leiomyomas or fibroids) are monoclonal, generally benign, smooth muscle tumors of the myometrium, the muscular portion of the uterus composed of smooth muscle and connective tissue. While these tumors are generally benign, they nonetheless can cause a variety of troubling symptoms. For example, uterine leiomyomata can cause pain in the lower back and abdomen, excessive menstrual bleeding (both in terms of volume and length of menstrual periods or bleeding between menses resulting in anemia and fatigue), pressure on the urinary bladder resulting in frequent urination and/or pressure on the rectum causing constipation. Large leiomyomata can press on the ureters (tubes going from the kidneys to the bladder) causing obstruction or blockage of urine which can lead to kidney damage. Uterine leiomyomata also can cause infertility. In some cases, uterine leiomyomata can cause infertility by impairing the uterine lining, blocking the fallopian tubes, or altering the position of the cervix, thus inhibiting sperm from reaching the uterus.

Uterine leiomyomata are common. Some studies suggest that about 20% to about 30% of all women over the age of 30 have leiomyomata, and an estimated 50% to about 75% of African American women have leiomyomata. Fibroids: An Overview of Diagnosis and Treatment, www.womenshealth-services.com (last visited Dec. 12, 2005). Other studies have found that uterine leiomyomata are clinically apparent in about 25% to about 50% of women (Buttram & Reiter, 36 Fertil. Steril. 433-45 (1981)), although careful pathologic examination of the uterus suggests that the prevalence may be as high as about 80%. Cramer & Patel, 94 Am. J. Clin. Pathol. 435-38 (1990).

The severity of symptoms associated with uterine leiomyomata, as well as their prevalence, requires a treatment for this condition. Previously, the only effective treatment for uterine leiomyomata was hysterectomy, an unacceptable treatment option for many women.

Because hysterectomy is an unacceptable treatment option for many women, other procedures have been developed. For example, myomectomy, the surgical removal of leiomyomata from the uterus was developed as an alternative in some cases. Uterine artery embolization has also been developed. In this radiologic procedure, uterine arteries are partially blocked, thus decreasing blood flow to the uterine leiomyomata inhibiting their growth and/or survival.

Myomectomy can be an effective treatment in some patients, however, there are risks associated with it. Some of these risks include scarring and infection. In some cases, scarring after myomectomy can lead to infertility. Studies of the effectiveness of uterine artery embolization have indicated that most subjects have a significant decrease in bleeding symptoms, as well as a reduction in uterine size. However, uterine artery embolization may also have serious consequences including infection, massive uterine bleeding, and uterine necrosis, requiring emergency surgery. Barbieri, 42 Clin. Obstet. Gynecol. 196-205 (1999). Subjects can also experience significant uterine pain, ischemia, and hypoxic changes following embolization. American College of Obstetricians and Gynecologists (ACOG) Practice Bulletin, No. 16 (May 2000). Based on these negative effects, a need for an acceptable treatment option for uterine leiomyomata remains.

Although the mechanisms leading to uterine leiomyomata tumorogenesis are not completely understood, evidence suggests that the development of uterine leiomyomata is ovarian steroid dependent. Murphy et al., 76(2) J. Clin. Endocrinol. 513-517 (2005) and Buttram et al., 36 Fertil. Steril. 433 (1981) which are both incorporated herein by reference. Part of this evidence comes from the findings that uterine leiomyomata contain both estrogen and progesterone receptors (Wilson et al., 55 Obstet. Gynecol. 20-4 (1980); Soules & McCarty 143 Am. J. Obstet. Gynecol. 6-11 (1980)) and that both of these hormones are thought to be involved in tumor formation. See www.womenshealthservices.com, supra. Further, estrogen and growth hormone are thought to act synergistically to stimulate leiomyomata growth as the two are elevated during pregnancy when the growth of leiomyomata is rapid. That progesterone may play a role in uterine leiomyomata growth is suggested by the finding of increased mitotic count in leiomyomata obtained during the secretory phase than in the proliferative phase of the menstrual cycle. Kawaguchi et al. 160 Am. J. Obstet. Gynecol. 637 (1988). Additionally, when the GnRH-agonist and a progesterone were co-administered, the expected regression of leiomyomata size seen with GnRH-agonist alone is not achieved. Friedman et al., 49 Fertil. Steril. 404 (1988); Wilson et al., 55 Obstet. Gynecol. 22 (1980); Soules et al., 143 Am. J. Obstet. Gynecol. 6 (1982). In addition to endogenous hormones, xenoestrogens in the environment (e.g., organochlorine pesticides, pharmacologic compounds) are also of potential concern as these environmental estrogens have been shown to promote the growth of uterine leiomyomata. Uterine Fibroids, www.raysahelian.com/fibroids (last visited Dec. 12, 2005).

Based on the foregoing, the potential for treating uterine leiomyomata by manipulating endogenous hormone levels emerged. One such treatment involves the use of gonadotropin releasing hormone agonists (GnRH agonists such as Lupron®, Synarel® or Zoladex®) which induce a low-estrogen state. Medical Treatment for Fibroids, www.fibroids.net (last visited Dec. 12, 2005). GnRH agonist treatment has been shown to reduce uterine volume by about 50% after about three months of GnRH agonist therapy. Id. GnRH agonist treatment has also been shown to stop menstrual flow (amenorrhea) allowing women with bleeding-induced anemia to significantly increase their iron stores. Id. Unfortunately, cessation of GnRH agonist treatment is followed by a rapid regrowth of uterine leiomyomata and of the uterus to pretreatment volume. Id. Additionally, because bone health also requires estrogen, long term use of GnRH agonists can significantly decrease bone density and can lead to bone loss or osteoporosis. Id. Currently, therefore, use of GnRH agonists alone for treatment of uterine leiomyomata is usually limited to a short one to three month preoperative course to shrink the uterus to facilitate a surgical procedure or to induce amenorrhea to improve hematologic condition before surgery. Id.

The use of anti-progestational agents as a treatment for uterine leiomyomata has also emerged. Mifepristone (RU-486; also sold by Danco Laboratories, Inc. under the tradename Mifeprex®) is an anti-progestational agent with anti-progesterone and antiglucocorticoid effects that binds to progesterone receptors more competitively than progesterone itself, thus blocking the actions of progesterone. The inhibition of progesterone triggers the shedding of the uterine wall, much like a normal menstruation.

Mifepristone has been shown to produce an equivalent amount of uterine shrinkage and rates of amenorrhea to GnRH agonists. Kettel et al., 60 Fertil. Steril. 642-46 (1993); Murphy et al., 76 J. Clin. Endocrinol. Metab. 513-17 (1993); Murphy et al., 64 Fertil. Steril. 187-90 (1995). Mifepristone has also been shown to reduce uterine leiomyomata size. Eisinger et al., 101(2) Obstet. Gynecol. 243-50 (2003). Thus, clinical studies of mifepristone for the treatment of uterine leiomyomata have suggested that mifepristone can result in symptomatic improvement. These studies, however, have recommended using doses of mifepristone such as 50 mg or 10 mg. Eisinger et al., supra; Murphy et al., supra. One study has confirmed the effectiveness of mifepristone at 5 mg when administered for 6 months. Eisinger et al., supra. While these doses of mifepristone can help to treat uterine leiomyomata, there are problems associated with them. For example, the highest described doses, such as 50 mg, can increase the prevalence and severity of hot flashes, can cause an elevation in hepatic enzymes and in some cases, due to mifepristone's antiglucocorticoid activity can result in deleterious side effects including, without limitation, glucocorticoid deprivation in the tissue and the pituitary gland resulting in an increase in serum ACTH and cortisol, as well as overt symptoms including complaints of anorexia, nausea, dizziness, weakness and somnolence. While the lower described doses, such as 10 mg, can cause less severe drawbacks, these doses can still be associated with side effects such as increased hot flashes, potentially interfering with patient compliance. Therefore, a need exists for a uterine leiomyomata treatment that is not associated with these drawbacks. A need also exist for treatments for other progesterone-related disorders that are not associated with these drawbacks.

SUMMARY OF THE INVENTION

Methods, dosing regimens and medications have now been discovered which provide a means for treating progesterone-related disorders but with a markedly lower dosage level or shorter time period of administration than employed previously. These methods, dosing regimens and medications can treat progesterone-related disorders at doses that avoid or lessen the occurrence or severity of adverse side effects found at higher doses. In one embodiment, the low-dose methods, dosing regimens and medications of the present invention are used to treat uterine leiomyomata.

Specifically, and in one embodiment, the present invention shows that about 2.5 mg mifepristone provides an effective treatment dosage for progesterone-related disorders. The present invention also shows that about 5.0 mg mifepristone provides an effective treatment dosage for progesterone-related disorders when administered for about one month. These lower dosages and/or shorter time periods of administration can have fewer or less severe side effects and adverse reactions than those observed with previously-used higher doses and/or longer time periods of treatment. Doses as low as 1.0 mg or below can also provide effective treatments for progesterone-related disorders.

One embodiment of the present invention includes a method comprising administering an anti-progestational agent to a patient in an amount that is less than 5.0 mg.

In some embodiments of the methods of the present invention, the less than 5.0 mg amount of the anti-progestational agent that is administered is selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In some embodiments of the methods of the present invention, the less than 5.0 mg amount of the anti-progestational agent is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In some embodiments, the less than 5.0 mg amount of the anti-progestational agent is administered to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

Additional embodiments of the present invention include methods comprising administering an anti-progestational agent to a patient for a duration of less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, and less than about 1 week.

In another embodiment of the methods of the present invention, an anti-progestational agent is administered to a patient for a duration of less than one month.

In some embodiments of the methods of the present invention, the anti-progestational agent that is administered for less than about 10 weeks is administered in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In further embodiments of the methods of the present invention, the anti-progestational agent that is administered for less than about 10 weeks is administered in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In some embodiments, an anti-progestational agent is administered to a patient for less than about 10 weeks to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

Another embodiment of the present invention includes a method comprising administering an anti-progestational agent to a patient in an amount of about 0.1 mg to about 0.2 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the patient weighs more than 110 pounds.

In another embodiment of the methods of the present invention, the anti-progestational agent is selected from one or more of the group consisting of mifepristone, onapristone, lilopristone, ZK 112.993, Org 31710, Org 33628, Org 31806, CDB-2914, CDB-4124, RJW, asoprisnil, J900, J956, J912 and J1042. In another embodiment of the methods of the present invention, the anti-progestational agent is mifepristone. In an additional embodiment of the methods of the present invention, the anti-progestational agent is not mifepristone.

In another embodiment of the methods of the present invention, the anti-progestational agent is an progesterone receptor active antagonist selected from one or more of the group consisting of mifepristone, onapristone, Org 31710, Org 31806, RTI-3021-012, and RTI-3021-022. In an additional embodiment, the anti-progestational agent is not mifepristone.

In another embodiment of the methods of the present invention, the one or more anti-progestational agents is administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the methods of the present invention, the one or more anti-progestational agents is administered to shrink uterine leiomyomata before a surgical treatment. In another embodiment of the methods of the present invention, the surgical treatment is selected from the group consisting of hysterectomy, myomectomy, uterine artery embolization and endometrial ablation.

In another embodiment of the methods of the present invention, the one or more anti-progestational agents is administered concurrently with a treatment selected from the group consisting of depo-provera acetate to treat breakthrough bleeding and/or intermittent bleeding, levonorgestrel containing IUDs to treat breakthrough bleeding and/or intermittent bleeding and cortisol or synthetic cortisol-like bioactive agents to treat excessive adrenal secretions.

In another embodiment of the methods of the present invention, the one or more anti-progestational agents is administered daily. In another embodiment of the methods of the present invention, the mifepristone is administered daily. In another embodiment of the methods of the present invention, the one or more anti-progestational agents is administered intermittently. In another embodiment of the methods of the present invention, the mifepristone is administered intermittently.

In another embodiment of the methods of the present invention, the administration route is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the methods of the present invention, the administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the methods of the present invention, the form is a sustained release form.

In another embodiment of the methods of the present invention, the patient is a pre-menopausal female over the age of 18. In another embodiment of the methods of the present invention, the patient has at least one uterine leiomyomata that is ≧2.5 cm in size. In another embodiment of the methods of the present invention, the patient has a total uterine volume of ≧160 cc.

In another embodiment of the methods of the present invention, the method further comprises administering a maintenance dose to the patient after a round of treatment has been completed.

The present invention also comprises dosing regimens. In one embodiment of the dosing regimens of the present invention, the dosing regimen comprises an anti-progestational agent that is directed to be administered to a patient in an amount that is less than 5.0 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the dosing regimens of the present invention, the less than 5.0 mg amount of the anti-progestational agent that is directed to be administered is selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In another embodiment of the dosing regimens of the present invention, the less than 5.0 mg amount of the anti-progestational agent that is directed to be administered is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

Another embodiment of the dosing regimens of the present invention comprises an anti-progestational agent that is directed to be administered to a patient for less than one month.

Another embodiment of the dosing regimens of the present invention comprises an anti-progestational agent that is directed to be administered to a patient for a duration selected from the group consisting of less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, and less than about 1 week.

Another embodiment of the dosing regimens of the present invention comprises an anti-progestational agent that is directed to be administered to a patient for less than one month to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the dosing regimens of the present invention, the anti-progestational agent that is directed to be administered for less than one month is administered in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In another embodiment of the dosing regimens of the present invention, the anti-progestational agent that is directed to be administered for less than one month is administered in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

Another embodiment of the dosing regimens of the present invention comprises an anti-progestational agent that is directed to be administered to a patient in an amount of about 0.1 mg to about 0.2 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the patient weighs more than 110 pounds.

In another embodiment of the dosing regimens of the present invention, the anti-progestational agent is selected from one or more of the group consisting of mifepristone, onapristone, lilopristone, ZK 112.993, Org 31710, Org 33628, Org 31806, CDB-2914, CDB-4124, RJW, asoprisnil, J900, J956, J912 and J1042. In another embodiment of the dosing regimen of the present invention, the anti-progestational agent is mifepristone. In an additional embodiment, the anti-progestational agent is not mifepristone.

In another embodiment of the dosing regimens of the present invention, the anti-progestational agent is a progesterone receptor active antagonist selected from one or more of the group consisting of mifepristone, onapristone, Org 31710, Org 31806, RTI-3021-012, and RTI-3021-022. In an additional embodiment, the anti-progestational agent is not mifepristone.

In another embodiment of the dosing regimens of the present invention, the one or more anti-progestational agents is directed to be administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the dosing regimens of the present invention, the one or more anti-progestational agents is directed to be administered to shrink uterine leiomyomata before a surgical treatment. In another embodiment of the dosing regimens of the present invention, the surgical treatment is selected from the group consisting of hysterectomy, myomectomy, uterine artery embolization, and endometrial ablation.

In another embodiment of the dosing regimens of the present invention, the one or more anti-progestational agents is directed to be administered concurrently with a treatment selected from the group consisting of depo-provera acetate to treat breakthrough bleeding and/or intermittent bleeding, levonorgestrel containing IUDs to treat breakthrough bleeding and/or intermittent bleeding and cortisol or synthetic cortisol-like bioactive agents to treat excessive adrenal secretions.

In another embodiment of the dosing regimens of the present invention, the one or more anti-progestational agents is directed to be administered daily. In another embodiment of the dosing regimens of the present invention, the mifepristone is directed to be administered daily. In another embodiment of the dosing regimens of the present invention, the one or more anti-progestational agents is directed to be administered intermittently. In another embodiment of the dosing regimens of the present invention, the mifepristone is directed to be administered intermittently.

In another embodiment of the dosing regimens of the present invention, the directed administration route is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the dosing regimens of the present invention, the administration is directed to occur through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the dosing regimens of the present invention, the form is a sustained release form.

In another embodiment of the dosing regimens of the present invention, the patient is a pre-menopausal female over the age of 18. In another embodiment of the dosing regimen of the present invention, the patient has at least one uterine leiomyomata that is ≧2.5 cm in size. In another embodiment of the dosing regimen of the present invention, the patient has a total uterine volume of ≧160 cc.

In another embodiment of the dosing regimens of the present invention, the dosing regimen further comprises a maintenance dose that is directed to be administered to the patient after a first round of treatment has been completed.

The present invention also comprises medications. In one embodiment, the medication of the present invention is an anti-progestational agent that is administered to a patient in an amount that is less than 5.0 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

Another embodiment of the medications of the present invention includes a medication that is an anti-progestational agent that is administered to a patient for less than one month to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

Another embodiment of the medications of the present invention includes a medication that is an anti-progestational agent that is administered to a patient in an amount of about 0.1 mg to about 0.2 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the patient weighs more than 110 pounds.

In another embodiment of the medications of the present invention, the anti-progestational agent is selected from one or more of the group consisting of mifepristone, onapristone, lilopristone, ZK 112.993, Org 31710, Org 33628, Org 31806, CDB-2914, CDB-4124, RJW, asoprisnil, J900, J956, J912 and J1042. In another embodiment of the medications of the present invention, the anti-progestational agent is mifepristone. In an additional embodiment, the anti-progestational agent is not mifepristone.

In another embodiment of the medications of the present invention, the anti-progestational agent is a progesterone receptor active antagonist selected from one or more of the group consisting of mifepristone, onapristone, Org 31710, Org 31806, RTI-3021-012, and RTI-3021-022. In an additional embodiment, the anti-progestational agent is not mifepristone.

In another embodiment of the medications of the present invention, the medication is administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the medications of the present invention, the medication is administered to shrink uterine leiomyomata before a surgical treatment. In another embodiment of the medications of the present invention, the surgical treatment is selected from the group consisting of hysterectomy, myomectomy, uterine artery embolization and endometrial ablation.

In another embodiment of the medications of the present invention, the medication is administered concurrently with a treatment selected from the group consisting of depo-provera acetate to treat breakthrough bleeding and/or intermittent bleeding, levonorgestrel containing IUDs to treat breakthrough bleeding and/or intermittent bleeding and cortisol or synthetic cortisol-like bioactive agents to treat excessive adrenal secretions.

In another embodiment of the medications of the present invention, the medication is administered daily. In another embodiment of the medications of the present invention, the medication is mifepristone and is administered daily. In another embodiment of the medications of the present invention, the medication is administered intermittently. In another embodiment of the medications of the present invention, the medication is mifepristone and is administered intermittently.

In another embodiment of the medications of the present invention, the administration route of the medication is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the medications of the present invention, the medication is in a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the medications of the present invention, the medication is in a sustained release form.

In another embodiment of the medications of the present invention, the medication is given to a patient that is a pre-menopausal female over the age of 18. In another embodiment of the medications of the present invention, the medication is given to a patient that has at least one uterine leiomyomata that is $\geq 2.5$ cm in size. In another embodiment of the medications of the present invention, the medication is given to a patient that has a total uterine volume of $\geq 160$ cc.

In another embodiment of the medications of the present invention, the medication comprises a maintenance dose to be administered after one of the above described methods or dosing regimens. In another embodiment of the medications of the present invention, the maintenance dose comprises mifepristone. In another embodiment of the medications of the present invention, the maintenance dose is selected from the group consisting of about 0.1 mg, 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg. In another embodiment of the medications of the present invention, the maintenance dose is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the medications of the present invention, the first round of treatment is selected from the group consisting of the use of an anti-progestational agent to treat uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the medications of the present invention, the maintenance dose is administered concurrently with a treatment selected from the group consisting of depo-provera acetate to treat breakthrough bleeding or intermittent bleeding, levonorgestrel (or agents similar to levonorgestrel) containing IUDs to treat breakthrough bleeding or intermittent bleeding and cortisol or synthetic cortisol-like bioactive agents to treat excessive adrenal secretions.

In another embodiment of the medications of the present invention, the maintenance dose is administered daily. In another embodiment of the medications of the present invention, the maintenance dose is administered intermittently.

In another embodiment of the medications of the present invention that contain a maintenance dose, the medication's administration route is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the medications with a maintenance dose of the present invention, the administration of the medication occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the medications with a maintenance dose of the present invention, the administration of the medication occurs through a sustained release form.

In another embodiment of the medications with a maintenance dose of the present invention, the medication is administered to a pre-menopausal female over the age of 18.

In another embodiment of the medications with a maintenance dose of the present invention, the medication is administered to a patient that has at least one uterine leiomyomata that is ≧2.5 cm in size.

In another embodiment of the medications with a maintenance dose of the present invention, the medication is administered to a patient that has a total uterine volume of ≧160 cc.

In another embodiment of the medications with a maintenance dose of the present invention, the medication comprises an anti-progestational agent that is directed to be administered to a patient in an amount that is less than 5.0 mg to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the medications with a maintenance dose of the present invention, the medication comprises an anti-progestational agent that is directed to be administered to a patient for less than one month to treat a non-malignant gynecological disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

The present invention also includes business methods. One embodiment of the business methods of the present invention comprises providing to a consumer an anti-progestational agent and a dosing regimen wherein the dosing regimen directs the anti-progestational agent to be administered to a patient in an amount that is less than 5.0 mg to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the business methods of the present invention, the method comprises providing to a consumer an anti-progestational agent and a dosing regimen wherein the dosing regimen directs the anti-progestational agent to be administered for less than one month to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the business methods of the present invention, the dosing regimen directs the anti-progestational agent to be administered in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In another embodiment of the business methods of the present invention, the dosing regimen directs the anti-progestational agent to be administered in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the business methods of the present invention, the dosing regimen directs that the anti-progestational agent that is administered for less than one month be administered in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In another embodiment of the business methods of the present invention, the dosing regimen directs that the anti-progestational agent that is administered for less than one month be administered in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the business methods of the present invention, the anti-progestational agent is selected from one or more of the group consisting of mifepristone, onapristone, lilopristone, ZK 112.993, Org 31710, Org 33628, Org 31806, CDB-2914, CDB-4124, RJW, asoprisnil, J900, J956, J912 and J1042. In another embodiment of the business methods of the present invention, the anti-progestational agents is mifepristone. In an additional embodiment, the anti-progestational agent is not mifepristone.

In another embodiment of the business methods of the present invention, the anti-progestational agent is selected from one or more of the group consisting of mifepristone, onapristone, Org 31710, Org 31806, RTI-3021-012, and RTI- 3021-022. In an additional embodiment, the anti-progestational agent is not mifepristone.

In another embodiment of the business methods of the present invention, the dosing regimen directs the anti-progestational to be administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the business methods of the present invention, the dosing regimen directs the anti-progestational to be administered to shrink uterine leiomyomata before a surgical treatment. In another embodiment of the business methods of the present invention, the surgical treatment is selected from the group consisting of hysterectomy, myomectomy, uterine artery embolization and endometrial ablation.

In another embodiment of the business methods of the present invention, the dosing regimen directs the anti-progestational to be administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the business methods of the present invention, the dosing regimen directs the anti-progestational to be administered daily. In another embodiment of the business methods of the present invention, the dosing regimen directs the anti-progestational to be administered intermittently.

In another embodiment of the business methods of the present invention, the dosing regimen directs the administration of the anti-progestational agent to be through a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the business methods of the present invention, the directed administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the business methods of the present invention, the form is a sustained release form.

In another embodiment of the business methods of the present invention, the patient is a pre-menopausal female over the age of 18. In another embodiment of the business methods of the present invention, the patient has at least one uterine leiomyomata that is ≧2.5 cm in size. In another embodiment of the business methods of the present invention, the patient has a total uterine volume of ≧160 cc.

In another embodiment of the business methods of the present invention, the dosing regimen further directs the administration of a maintenance dose of an anti-progestational agent to the patient after the completion of a first round of treatment. In another embodiment of the business methods of the present invention, the business method further comprises providing a maintenance dose of the anti-progestational agent to a consumer.

In another embodiment of the business methods of the present invention, the anti-progestational agent is mifepristone and the maintenance dose is selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg.

In another embodiment of the business methods of the present invention, the anti-progestational agent is mifepristone and the maintenance dose is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the business methods of the present invention, the dosing regimen directs daily administration of the maintenance dose. In another embodiment of the business methods of the present invention, the dosing regimen directs intermittent administration of the maintenance dose.

In another embodiment of the business methods of the present invention, the dosing regimen directs the administration of the maintenance dose to be through a route selected from selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the business methods of the present invention, the maintenance dose is provided in a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the business methods of the present invention, the maintenance dose is provided as a sustained release form.

In another embodiment of the business methods of the present invention, the dosing regimen directs the administration to occur in a pre-menopausal female over the age of 18. In another embodiment of the business methods of the present invention, the dosing regimen directs the administration to occur in a patient that has at least one uterine leiomyomata that is ≧2.5 cm in size. In another embodiment of the business methods of the present invention, the dosing regimen directs the administration to occur in a patient that has a total uterine volume of ≧160 cc.

In another embodiment, a business method is provided comprising the step of providing to a consumer an anti-progestational agent and a dosing regimen wherein the dosing regimen directs the anti-progestational agent to be administered to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer.

In an additional embodiment of the business methods of the invention, the anti-progestational agent is provided to a consumer in units of less than about 5.0 mg and the dosing regimen directs the anti-progestational agent to be administered in an amount less than 5.0 mg per day, or the anti-progestational agent is provided in units of less than about 2.5 mg and the dosing regimen directs the anti-progestational agent to be administered in an amount less than 2.5 mg per day, or the anti-progestational agent is provided in equivalent dosage units of less than about 1.25 mg of the anti-progestational agent and the dosing regimen directs the anti-progestational agent to be administered in an amount less than 1.25 mg per day. In another embodiment of the business methods of the invention, the anti-progestational agent is provided in an amount of less than about 40 units, and the dosing regimen directs the anti-progestational agent to be administered for less than one month.

In another embodiment of the business methods of the invention, the anti-progestational agent is selected from the group consisting of: mifepristone, onapristone, lilopristone, ZK 112.993, Org 31710, Org 33628, Org 31806, CDB-2914, CDB-4124, RJW, asoprisnil, J900, J956, J912 and J1042. In another embodiment of the business methods of the invention, the anti-progestational agent is mifepristone. In an additional embodiment, the anti-progestational agent is not mifepristone.

In another embodiment of the business methods of the invention, the dosing regimen directs the anti-progestational agent to be administered to the patient as a maintenance dose in an amount less than 2.5 mg after administering the anti-progestational agent in an amount less than 5 mg. In some embodiments of the business methods of the invention, the dosing regiment directs both the anti-progestational agent to be administered daily.

In another embodiment of the business methods of the invention, the anti-progestational agent is provided as a first set of equivalent dosage units, each comprising less than about 5.0 mg of the anti-progestational agent, and a second set of equivalent dosage units, each comprising less than about 2.5 mg of the anti-progestational agent.

Embodiments of the present invention also include methods, dosing regimens, medications, maintenance doses and business methods where mifepristone is excluded as an anti-progestational agent. For example, in one embodiment of the methods of the present invention the method comprises administering an anti-progestational agent to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the antiprogestational agent is not mifepristone.

In another embodiment of the non-mifepristone methods of the present invention, the anti-progestational agent is administered in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In another embodiment of the non-mifepristone methods of the present invention, the anti-progestational agent is administered in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the non-mifepristone methods of the present invention, the anti-progestational agent is selected from one or more of the group consisting of onapristone, lilopristone, ZK 112.993, Org 31710, Org 33628, Org 31806, CDB-2914, CDB-4124, RJW, asoprisnil, J900, J956, J912 and J1042.

In another embodiment of the non-mifepristone methods of the present invention, the anti-progestational agent is selected from one or more of the group consisting of mifepristone, onapristone, Org 31710, Org 31806, RTI-3021-012, and RTI-3021-022.

In another embodiment of the non-mifepristone methods of the present invention, the one or more anti-progestational agents is administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the non-mifepristone methods of the present invention, the one or more anti-progestational agents is administered to shrink uterine leiomyomata before a surgical treatment. In another embodiment of the non-mifepristone methods of the present invention, the surgical treatment is selected from the group consisting of hysterectomy, myomectomy, uterine artery embolization and endometrial ablation.

In another embodiment of the non-mifepristone methods of the present invention, the one or more anti-progestational agents is administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the non-mifepristone methods of the present invention, the anti-progestational agent is administered daily. In another embodiment of the non-mifepristone methods of the present invention, the anti-progestational agent is administered intermittently. In another embodiment of the non-mifepristone methods of the present invention, the administration is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone methods of the present invention, the administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone methods of the present invention, the form is prepared as a sustained release form.

In another embodiment of the non-mifepristone methods of the present invention, the patient is a pre-menopausal female over the age of 18. In another embodiment of the non-mifepristone methods of the present invention, the patient has at least one uterine leiomyomata that is $\geq 2.5$ cm in size. In another embodiment of the non-mifepristone methods of the present invention, the patient has a total uterine volume of $\geq 160$ cc.

In another embodiment of the non-mifepristone methods of the present invention, the method further comprises administering a maintenance dose to the patient after the completion of a first round of treatment.

Embodiments of the present invention also include nonmifepristone dosing regimens. In one embodiment of the dosing regimens of the present invention, the anti-progestational agent that is directed to be administered to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the antiprogestational agent is not mifepristone.

In another embodiment of the non-mifepristone dosing regimens of the present invention, the anti-progestational agent is directed to be administered to the patient in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In another embodiment of the non-mifepristone dosing regimens of the present invention, the anti-progestational agent is directed to be administered to the patient in an amount selected from the group consisting of about less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the non-mifepristone dosing regimens of the present invention, the anti-progestational agent is selected from one or more of the group consisting of onapristone, lilopristone, ZK 112.993, Org 31710, Org 33628, Org 31806, CDB-2914, CDB-4124, RJW, asoprisnil, J900, J956, J912 and J1042.

In another embodiment of the non-mifepristone dosing regimens of the present invention, the anti-progestational agent is selected from one or more of the group consisting of mifepristone, onapristone, Org 31710, Org 31806, RTI-3021-012, and RTI-3021-022.

In another embodiment of the non-mifepristone dosing regimens of the present invention, the one or more anti-progestational agents is directed to be administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the non-mifepristone dosing regimens of the present invention, the one or more anti-progestational agents is directed to be administered to shrink uterine leiomyomata before a surgical treatment. In another embodiment of the non-mifepristone dosing regimens of the present invention, the surgical treatment is selected from the group consisting of hysterectomy, myomectomy, uterine artery embolization and endometrial ablation.

In another embodiment of the non-mifepristone dosing regimens of the present invention, the one or more anti-progestational agents is directed to be administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the non-mifepristone dosing regimens of the present invention, the anti-progestational agent is directed to be administered daily. In another embodiment of the non-mifepristone dosing regimens of the present invention, the anti-progestational agent is directed to be administered intermittently.

In another embodiment of the non-mifepristone dosing regimens of the present invention, the directed administration is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone dosing regimens of the present invention, the directed administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone dosing regimens of the present invention, the form is prepared as a sustained release form.

In another embodiment of the non-mifepristone dosing regimens of the present invention, the patient is a pre-menopausal female over the age of 18. In another embodiment of the non-mifepristone dosing regimens of the present invention, the patient has at least one uterine leiomyomata that is $\geq 2.5$ cm in size. In another embodiment of the non-mifepristone dosing regimens of the present invention, the patient has a total uterine volume of $\geq 160$ cc.

In another embodiment of the non-mifepristone dosing regimens of the present invention, the dosing regimen further directs the administration of a maintenance dose to the patient after the completion of a first round of treatment.

The present invention also includes non-mifepristone medications. In one embodiment of the medications of the present invention comprises an anti-progestational agent and is administered to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery. In this embodiment the antiprogestational agent is not mifepristone.

In another embodiment of the non-mifepristone medications of the present invention, the medication includes a dosage of an anti-progestational agent selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In another embodiment of the non-mifepristone medications of the present invention, the medication includes a dosage of an anti-progestational agent selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the non-mifepristone medications of the present invention, the anti-progestational agent is selected from one or more of the group consisting of onapristone, lilopristone, ZK 112.993, Org 31710, Org 33628, Org 31806, CDB-2914, CDB-4124, RJW, asoprisnil, J900, J956, J912 and J1042.

In another embodiment of the non-mifepristone medications of the present invention, the anti-progestational agent is selected from one or more of the group consisting of mifepristone, onapristone, Org 31710, Org 31806, RTI-3021-012, and RTI-3021-022.

In another embodiment of the non-mifepristone medications of the present invention, the one or more anti-progestational agents is administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the non-mifepristone medications of the present invention, the one or more anti-progestational agents is administered to shrink uterine leiomyomata before a surgical treatment. In another embodiment of the non-mifepristone medications of the present invention, the surgical treatment is selected from the group consisting of hysterectomy, myomectomy, uterine artery embolization and endometrial ablation.

In another embodiment of the non-mifepristone medications of the present invention, the one or more anti-progestational agents is administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the non-mifepristone medications of the present invention, the anti-progestational agent is administered daily. In another embodiment of the non-mifepristone medications of the present invention, the anti-progestational agent is administered intermittently.

In another embodiment of the non-mifepristone medications of the present invention, the administration is selected from a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone medications of the present invention, the administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone medications of the present invention, the form is prepared as a sustained release form.

In another embodiment of the non-mifepristone medications of the present invention, the patient is a pre-menopausal female over the age of 18. In another embodiment of the non-mifepristone medications of the present invention, the patient has at least one uterine leiomyomata that is $\geq 2.5$ cm in size. In another embodiment of the non-mifepristone medications of the present invention, the patient has a total uterine volume of $\geq 160$ cc.

In another embodiment of the non-mifepristone medications of the present invention, medication comprises a maintenance dose of an anti-progestational agent that is administered after an anti-progestational agent is administered to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the anti-progestational agent is not mifepristone.

In another embodiment of the non-mifepristone medications of the present invention, the maintenance dose is selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg In another embodiment of the non-mifepristone medications of the present invention, the maintenance dose is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 or less than about 0.25 mg, and less than about 0.75 mg.

In another embodiment of the non-mifepristone medications of the present invention, the maintenance dose is administered after a first round of treatment selected from the group consisting of the use of an anti-progestational agent to treat uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

In another embodiment of the non-mifepristone medications of the present invention, the maintenance dose is administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the non-mifepristone medications of the present invention, the maintenance dose is administered daily. In another embodiment of the non-mifepristone medications of the present invention, the maintenance dose is administered intermittently.

In another embodiment of the non-mifepristone medications of the present invention, the medication's administration route is selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone medications of the present invention, the administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone medications of the present invention, the form is prepared as a sustained release form.

In another embodiment of the non-mifepristone medications of the present invention, the medication is administered to a pre-menopausal female over the age of 18. In another embodiment of the non-mifepristone medications of the present invention, the medication is administered to a patient that has at least one uterine leiomyomata that is $\geq 2.5$ cm in size. In another embodiment of the non-mifepristone medications of the present invention, the medication is administered to a patient that has a total uterine volume of $\geq 160$ cc.

The present invention also includes non-mifepristone business methods. In one embodiment of the methods of the present invention, the business method comprises providing to a consumer an anti-progestational agent and a dosing regimen wherein the dosing regimen directs the anti-progestational agent to be administered to a patient to treat a disorder selected from the group consisting of uterine leiomyomata, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery wherein the anti-progestational agent is not mifepristone.

In another embodiment of the non-mifepristone business methods of the present invention the anti-progestational agent is provided to a consumer in an amount selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In another embodiment of the non-mifepristone business methods of the present invention the anti-progestational agent is provided to a consumer in an amount selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 less than about 1.50 mg, less than about 1.25 mg, less than about 1.0 mg, less than about 0.75 mg, less than about 0.5 mg, or less than about 0.25 mg, and less than about 0.75 mg.

In another embodiment of the non-mifepristone business methods of the present invention the anti-progestational agent is selected from one or more of the group consisting of onapristone, lilopristone, ZK 112.993, Org 31710, Org 33628, Org 31806, CDB-2914, CDB-4124, RJW, asoprisnil, J900, J956, J912 and J1042.

In another embodiment of the non-mifepristone business methods of the present invention the anti-progestational agent is selected from one or more of the group consisting of mifepristone, onapristone, Org 31710, Org 31806, RTI-3021-012, and RTI-3021-022.

In another embodiment of the non-mifepristone business methods of the present invention the dosing regimen directs the anti-progestational to be administered after the conclusion of a treatment selected from the group consisting of the administration of birth control pills to treat severe dysmenorrhea, polymenorrhea or dysfunctional uterine bleeding, the administration of GnRh analogues to treat uterine leiomyomata or endometriosis, myomectomy to treat uterine leiomyomata, uterine artery embolization to treat uterine leiomyomata, endometrial ablation to treat menorrhagia or polymenorrhea and ultrasound therapy to treat uterine leiomyomata.

In another embodiment of the non-mifepristone business methods of the present invention the dosing regimen directs the anti-progestational to be administered to shrink uterine leiomyomata before a surgical treatment. In another embodiment of the business methods of the present invention the surgical treatment is selected from the group consisting of hysterectomy, myomectomy, uterine artery embolization and endometrial ablation.

In another embodiment of the non-mifepristone business methods of the present invention the dosing regimen directs the anti-progestational to be administered concurrently with a treatment selected from the group consisting of depo-provera acetate to treat breakthrough bleeding or intermittent bleeding, levonorgestrel containing IUDs to treat breakthrough bleeding or intermittent bleeding and cortisol or synthetic cortisol-like bioactive agents to treat excessive adrenal secretions.

In another embodiment of the non-mifepristone business methods of the present invention the dosing regimen directs the anti-progestational to be administered daily. In another embodiment of the non-mifepristone business methods of the present invention the dosing regimen directs the anti-progestational to be administered intermittently.

In another embodiment of the non-mifepristone business methods of the present invention the dosing regimen directs the administration to be through a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone business methods of the present invention the directed administration occurs through a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone business methods of the present invention the form is provided as a sustained release form.

In another embodiment of the non-mifepristone business methods of the present invention the dosing regimen directs the administration to occur in a pre-menopausal female over the age of 18. In another embodiment of the non-mifepristone business methods of the present invention the dosing regimen directs the administration to occur in a patient with at least one uterine leiomyomata that is $\geq 2.5$ cm in size. In another embodiment of the non-mifepristone business methods of the present invention the dosing regimen directs the administration to occur in a patient with a total uterine volume of $\geq 160$ cc.

In another embodiment of the non-mifepristone business methods of the present invention the dosing regimen further directs the administration of a maintenance dose of an anti-progestational agent to the patient after the completion of a first round of treatment.

In another embodiment of the non-mifepristone business methods of the present invention the business method further comprises providing a maintenance dose of the anti-progestational agent.

In another embodiment of the non-mifepristone business methods of the present invention the maintenance dose is selected from the group consisting of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg and about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In another embodiment of the non-mifepristone business methods of the present invention the maintenance dose is selected from the group consisting of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, and less than about 0.75 mg.

In another embodiment of the non-mifepristone business methods of the present invention the dosing regimen directs daily administration of the maintenance dose. In another embodiment of the non-mifepristone business methods of the present invention the dosing regimen directs intermittent administration of the maintenance dose.

In another embodiment of the non-mifepristone business methods of the present invention the dosing regimen directs the administration of the maintenance dose to be through a route selected from selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

In another embodiment of the non-mifepristone business methods of the present invention the maintenance dose is provided in a form selected from the group consisting of one or more of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray. In another embodiment of the non-mifepristone business methods of the present invention the form is provided as a sustained release form.

In another embodiment of the non-mifepristone business methods of the present invention the dosing regimen directs the administration of the maintenance dose to occur in a pre-menopausal female over the age of 18. In another embodiment of the non-mifepristone business methods of the present invention the dosing regimen directs the administration of the maintenance dose to occur in a patient that has at least one uterine leiomyomata that is ≧2.5 cm in size. In another embodiment of the non-mifepristone business methods of the present invention the dosing regimen directs the administration of the maintenance dose to occur in a patient that has a total uterine volume of ≧160 cc.

SUMMARY OF THE DRAWINGS

FIG. 1 is a table showing the characteristics of Study Subjects randomized to the treatment group (N=22) and the placebo group (N=20).

DETAILED DESCRIPTION OF THE INVENTION

Figure 2:
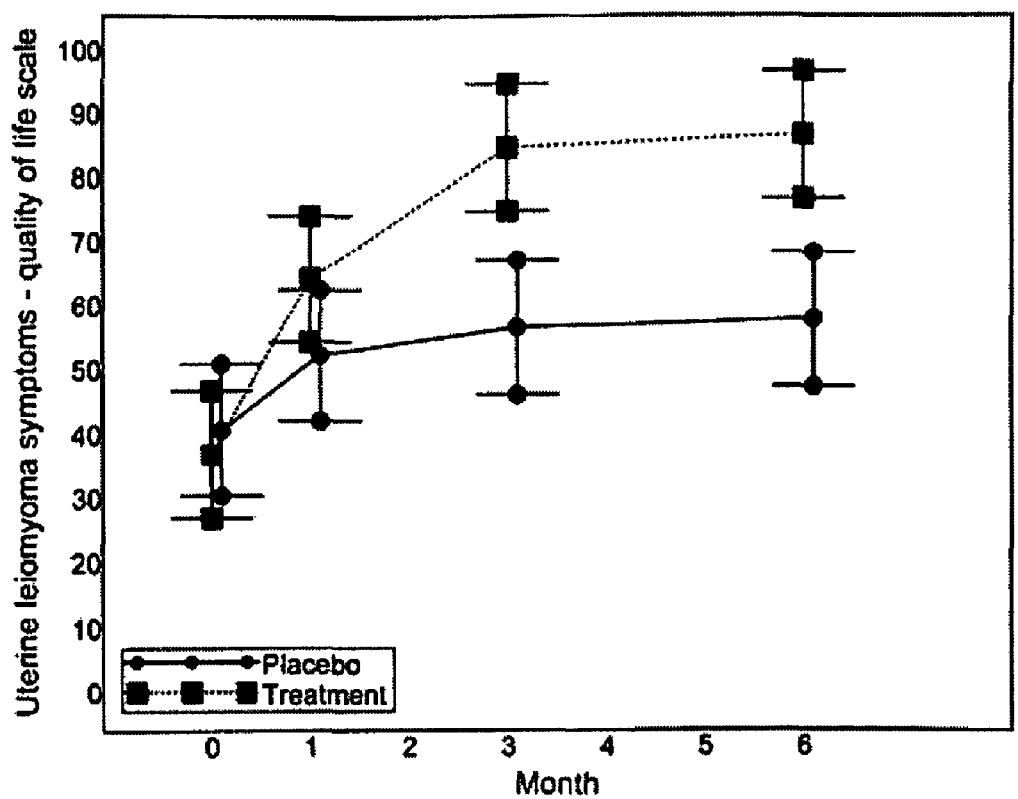
FIG. 2 is a graph showing the change in uterine leiomyoma-specific quality of life, measured using the total score on the Uterine Leiomyoma Symptom Quality of Life scale, as a function of treatment duration among mifepristone and placebo groups. Bars represent 95% confidence intervals surrounding the change in the score at each time point.

It is to be understood that the present invention is not limited to the particular embodiments, materials, and examples described herein, as these may vary. It is also to be understood that the terminology used herein is used for the purpose of describing particular embodiments only, and is not intended to limit the scope of the present invention. It must be noted that as used herein and in the appended embodiments, the singular forms "a," "an," and "the" include the plural reference unless the context clearly dictates otherwise. Thus, for example, a reference to "a disorder" or "a medication" is a reference to one or more disorders or medications and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

Prior to setting forth the invention in more detail, it may be helpful to provide an understanding of certain terms that will be used hereinafter.

The term "subject," as used herein, comprises any and all organisms and includes the term "patient." "Subject" may refer to a human or any other animal.

Breakthrough bleeding: As used herein, the phrase "breakthrough bleeding" includes vaginal bleeding or staining between menstrual periods that lasts for a short duration, generally less than about one hour.

Intermittent bleeding: As used herein, the phrase "intermittent bleeding" also includes vaginal bleeding between menstrual periods but that is more long-term than breakthrough bleeding. Generally, intermittent bleeding will last for more than about one hour.

Endometriosis: As used herein, "endometriosis" includes a disease in which functioning endometrial tissue is present in sites outside the uterine cavity. The disease is frequently characterized by progressive, disabling dysmenorrhea and pelvic pain around the time of the menses.

Induration includes the hardening of a normally soft tissue or organ due to inflammation, infiltration of a neoplasm or an accumulation of blood.

Dysmenorrhea: As used herein, "dysmenorrhea" refers to pain during menstruation or just before its onset. "Just before onset" refers to within about 24 hours before menstruation begins.

Severe dysmenorrhea: As used herein, the phrase "severe dysmenorrhea" includes pain that results in partial or total disability during or just before menstruation. "Disability" in this context refers to a reduction in normal activity levels.

Dyspareunia includes the occurrence of pain during sexual intercourse.

Dysfunctional Uterine Bleeding: As used herein, "dysfunctional uterine bleeding" includes a condition in which menstrual bleeding is abnormally heavy or occurs between periods. Dysfunctional uterine bleeding is also abnormal vaginal bleeding that occurs during a menstrual cycle that produced no egg (i.e. ovulation did not take place).

Adenomyomas: As used herein, "adenomyomas" includes abnormal invasions of the uterine fibrous and muscular layers by the endometrial lining.

Polymenorrhea: As used herein, "polymenorrhea" includes the occurrence of menstrual cycles at frequency that is higher than normal.

Menorrhagia: As used herein, "menorrhagia" includes excessive uterine bleeding occurring at the regular intervals of menstruation, the period of flow being of greater than usual duration.

Hirsutism: As used herein, "hirsutism" includes the growth of excessive hair in women on parts of the body where excessive hair is generally not present, without limitation, on the back and chest.

Concurrent Administration: As used herein, the term "concurrent administration" includes the meaning of overlapping in duration at least in part. Under this meaning, for two bioactive agents to be administered concurrently, their administration occurs within a certain desired time. The bioactive agent's administration may begin and end on the same day. The administration of one bioactive agent can also precede the administration of a second bioactive agent by one or more days as long as both bioactive agents are taken on the same day at least once. Similarly, the administration of one bioactive agent can extend beyond the administration of a second bioactive agent as long as both bioactive agents are taken on the same day at least once. The bioactive agents do not have to be taken at the same time each day to include concurrent administration.

Sequential Administration: As used herein, "sequential administration" includes that the administration of two bioactive agents do not occur on a same day.

Intermittent Administration: As used herein, "intermittent administration" includes the administration of a bioactive agent for a period of time ("first period of administration"), followed by a time during which the bioactive agent is not taken or is taken at a lower maintenance dose ("off-period") followed by a period during which the bioactive agent is administered again ("second period of administration"). Generally, during the second phase of administration, the dosage level of the bioactive agent will match that administered during the first period of administration. This protocol is not required, however, and for administration to be intermittent, the dosage administered during the second period of administration need only be larger than that received during the off-period.

Cortisol or synthetic cortisol-like bioactive agents: As used herein, the phrase "cortisol or synthetic cortisol-like bioactive agents" includes corticosteroids including mineralocorticosteroids (including, without limitation cortisol, deoxycorticosterone and flurohydrocortisone) and glucocorticoids (including, without limitation, beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide)).

Maintenance dose: As used herein, the phrase "maintenance dose" includes a dose of an administered medication that is lower than a previously administered dose of the same medication (or a variant thereof). A maintenance dose is intended to maintain the required concentration of medication in the body in order to help maintain a therapeutic effect obtained during earlier treatment. As will be described more fully below, a maintenance dose can be administered daily, more than once daily, weekly, more than once weekly, monthly, more than once monthly, yearly, more than once yearly and can include a set, alternating or changing number of times per day, per week, per month or per year.

First Round of Treatment: As used herein, the phrase "first round of treatment" includes a first course of action prescribed by a health care provider. In the present use, the first round of treatment will include the prescription or administration of at least one bioactive agent although the first round of treatment may also include other procedures. The prescribed or administered bioactive agent will be at a higher dose than a later maintenance dose that can be given during a second round of treatment. In some cases, a health care provider may evaluate the effectiveness of the first course of action at the end of a first round of treatment, however, such an evaluation is not required and a health care provider may prescribe a first round of treatment and a second round of treatment (including a maintenance dose) at the same time before evaluating effectiveness of the first round of treatment. In this situation, the first round of treatment will include the prescription or administration of at least one bioactive agent (although the first round of treatment may also include other procedures) for a period of time, followed by a second round of treatment that can include the prescription or administration of the same bioactive agents at a lower dose or one or more different bioactive agents or procedures.

Birth Control Pills: As used herein, the phrase "birth control pills" include all therapies that deliver a combination of estrogen and progesterone and reduce the likelihood of ovulation. While the term "pill" is included in the phrase, a pill is not required under the adopted definition and any administration route can be included under the definition.

Treat and Treatment: As used herein, the terms "treat" and "treatment" can include both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms, diminishment of extent of a condition, disorder or disease, stabilized (i.e., not worsening) state of condition, disorder or disease, delay in onset or slowing of condition, disorder or disease progression, amelioration of the condition, disorder or disease state, remission (whether partial or total) or enhancement or improvement of condition, disorder or disease. Treatment can also include eliciting a clinically significant response, without excessive levels of side effects. Treatment can also include prolonging survival as compared to expected survival if not receiving treatment.

As stated earlier, progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which modulate the effects of progesterone can be useful in treating a variety of disease states and conditions.

Methods are provided herein for the treatment of progesterone-related conditions, wherein the methods comprise administering one or more anti-progestational agents. The anti-progestational agent(s) may comprise any agent that modulates the effect of progesterone in the subject targeted for treatment, directly and/or indirectly, including but not limited to, chemical compounds, proteins, peptidomimetics, antisense molecules, ribozymes and other nucleic acids. In various embodiments, the anti-progestational agent may comprise a compound that modulates progesterone receptor activity, such as a progesterone receptor antagonist (e.g., an agent that inhibits one or more responses characteristic of progesterone receptor activation); a progesterone receptor inverse agonist (e.g., an agent that blocks or inhibits a constitutive progesterone receptor activity); and/or an allosteric progesterone receptor modulator (e.g., an agent that binds to a site distinct from the ligand-binding site, and modulates the response of an endogenous ligand, co-activator or co-repressor, and/or other receptor modulator). In some embodiments, the activity of progesterone receptor modulator requires one or more additional co-factors or other agents.

A number of compounds have been developed to act as anti-progestational agents. Some of these agents are progesterone antagonists, including but not limited to: mifepristone (RU 486; 17-hydroxy-11-(4-dimethylaminophenyl)-17-(prop-1-ynyl)estra-4,9-dien-3-one; RU 46556 [11β-(4-dimethylaminophenyl)-17β-hydroxy-17α-(3-methyl-1-butynyl)-4,9-estradien-3-one]; RU 49295 [11β-(4-acetophenyl)-17β-hydroxy-17α-(3-methyl-1-butynyl)-4,9-estradien-3-one]; β-[(4-N,N-dimethyl amino)-phenyl]-17β-hydroxy-17α-propynyl-4,9(10)-oestradiene-3-one); onapristone (ZK 98.299); ZK 112.993[11-4(4-acetylphenyl)-17-hydroxy-17-(-propynyl)-,9-diene-3-one]; Org 31710 [(6α,11β,17β)-11-(4-NMe$_2$-phenyl)-6-Me-4',5'-dihydrospiro[oestra-4,9-diene-17,2(3'H)-furan]-3-one]; Org 33628 [(11β,17α)-(4-acetylphenyl)-17,23-epoxy-19,24-dinorchola-4,9,20-trien-3-one]; Org 31806 [(7β,11β,17β)-11-(4-NMe$_2$-phenyl)-7-Me-4',5'-dihydrospiro(oestra-4,9-diene-17,2'(3'H)-furan)-3-one]; and lilopristone (ZK 98734); CDB-2914 (17α-acetoxy-11β-[4-N,N-dimethylaminophenyl]-19-norpregna-4,9-diene-3,20-dione); CDB-4124 (17α-acetoxy-21-methoxy-11β-[4-N,N-dimethylaminophenyl]-19-norpregna-4,9-diene-3,20-dione) and RJW compound. Compounds that have previously been designated J867 (asoprisnil), J900, J956, J912 (major metabolite of asoprisnil), J914, and J1042 are all also suitable for use in accordance with the methods provided herein. Such compounds include, without limitation, [4-[17β-Methoxy-17α-(methoxymethyl)-3-oxoestra-4,9-dien-11β-yl]benzaldehyd-(1E)-oxim]; and [4-17β-Hydroxy-17-α-(methoxymethyl)-3-oxoestra-4,9-dien-11β-yl]benzaldehyd-(1E)-oxim]; [4-17β-Methoxy-17α-(methoxymethyl)-3-oxoestra-4,9-dien-11β-yl]benzaldehyd-(1E)-[O-(ethoxy)carbonyl]oxim; [4-17β-Methoxy-17α-(methoxymethyl)-3-oxoestra-4,9-dien-11β-yl]benzaldehyd-(1E)-(O-acetyl)oxim]; and [4-[17β-Methoxy-17α-(methoxymethyl)-3-oxoestra-4,9-dien-11β-yl]benzaldehyd-(1E)-[O-(ethylamino)carbonyl)oxim]. These and other potentially useful agents are described in, e.g., the following publications: the aforementioned PCT applications WO 93/21926 and WO 93/21927; U.S. Pat. No. 4,386,085; U.S. Pat. No. 4,027,019; U.S. Pat. No. 4,000,273; U.S. Pat. No. 3,890,356; U.S. Pat. No. 3,622,622; U.S. Pat. No. 3,983,144; U.S. Pat. No. 3,462,466; U.S. Pat. No. 3,790,564; U.S. Pat. No. 4,231,946; Pollow, et al., Contraception 40:213-32 (1989); Cook et al., Hum Reprod.; 9 Suppl 1:32-9 (1994); Hazra et al., Steroids. 65(3): 157-62 (2000); and Michna et al., supra, the entire disclosures of which are hereby incorporated by reference.

Regarding mifepristone specifically, this compound is a synthetic 19-nonsteroid, lacking the C19-methyl group of natural progesterone (P) and glucocorticosteroids (G). The bioactive agent has been found to have a high affinity for both the progesterone receptor (PR) and the glucocorticosteroid receptor (GR) and has strong antiprogesterone and antiglucocorticosteroid activity. Its contragestational properties and clinical applications have been reviewed by Baulieu, 245 Science 1351 (1989) which is incorporated herein by reference. Mifepristone is commercially available in a number of countries and is exclusively available in the United States under the tradename Mifeprex® (Danco Laboratories, Inc.).

In some embodiments, the anti-progestational agent is a nonsteroidal progesterone receptor antagonist, such as LG120753, LG120830, LG100127, RWJ26329, CP8400, CP8401 and compounds described in Pooley et al., J Med Chem, 41: 3461-3466 (1998), Zhi et al., Bioorgan Med Chem Lett, 10: 415-418 (2000), Palmer et al., J Steroid Biochem Mol Biol 75: 33-42 (2000), Tabata et al., Eur J Pharm, 430: 159-165 (2001), Dukes et al., Steroids, 65: 725-731 (2000), Kang et al., Bioorg Med Chem Lett., Epub (2007), Combs et al., J Med Chem, 38: 4878-4879 (1995), and U.S. Pat. App. No. 20050085470 to Zhang et al.

Also contemplated as within the scope of the present invention are inhibitors or antagonists of progesterone which modulate the production, metabolism, and/or transport of progesterone. Examples of suitable progesterone synthesis inhibitors include, but are not limited to: trilostane, epostane, azastene and cyanoketone. See, for example, WO 93/21926, WO 93/21927 and Haider & Inbaraj, 73 Gen Comp Endocrinol, 92-5 (1989).

To identify additional anti-progestational agents suitable for use in the methods, dosing regimens and medications of the present invention, it is further possible to employ heretofore-known biological assays for such agents. An exemplary assay is described in Michna, H. et al., 38 J. Steroid Biochem. Molec. Biol. 359-65 (1991) for progesterone antagonists. In this bioassay rats are subjected to ovariectomy on day 1. On day 8 the experimental rats are administered estrone, progesterone and the progesterone antagonist daily. On day 11 the animals are sacrificed and the number of tubular alveolar buds in the inguinal mammary gland counted in a whole mount preparation using a 40-fold magnification. Potent progesterone antagonists inhibit the proliferative action of the progesterone and reduce the number of tubular alveolar buds by 30 to 35% or more.

In some embodiments, the anti-progestational agent is selected from the group consisting of mifepristone, onapristone, Org 31710, Org 31806, RTI-3021-012, and RTI-3021-022. Without being bound by any particular theory, it is believed that these and other compounds act as "active antagonists" at progesterone receptor(s), in that they not only compete with endogenous ligands/agonists for binding to progesterone receptors, but also exert additional effects that further antagonize progesterone receptor activity and/or the effects thereof. For example, after competing with endogenous agonists for progesterone receptor binding, mifepristone, onapristone, and other active antagonists enter the nucleus as an antagonist-receptor complex and compete with agonist-bound receptors for DNA transcriptional control sites, such as progesterone response elements (PREs), recruit additional co-factors (e.g., co-repressors), and/or exert other effects that antagonize progesterone receptor function.

In some embodiments, the anti-progestational agent is a compound identified as being an active progesterone receptor antagonist by an assay method that detects, directly or indirectly, one or more of the agent's activities, in addition to progesterone receptor binding. In some embodiments, the anti-progestational agent is capable of binding to one or more DNA elements targeted by progesterone receptor agonists, as described, e.g., in Gass et al., Endocriol., 139: 1905-1919 (1998) and/or recruiting co-repressors or other co-factors that inhibit progesterone receptor activity, as described, e.g., in Zhang et al., Mol Endocrinol, 12: 513-524 (1998) and Wagner et al., Mol Cell Biol, 18: 1369-1378 (1998). In further embodiments, the anti-progestational agent, alone or bound to a progesterone receptor or other molecule, is capable of heterodimerizing with agonist-bound progesterone receptors, as described, e.g., in DeMarzo et al., Biochemistry, 31:10491-10501 (1992) and Leonhardt et al., Mol Endocrinol, 12: 1914-1930 (1998). In some embodiments, the anti-progestational agent is a active antagonist against progesterone receptors and a competitive antagonist against glucocorticoid receptors, such as the anti-progestational agents RTI-012, RTI-022, and compounds described in Wagner et al., Endocrinol, 140: 1449-1458 (1999).

In some embodiments, the anti-progestational agent receptor is non-selective in its effects against progesterone receptor subtypes A and B (PR-A and PR-B, respectively), whereas in other embodiments the anti-progestational agent exhibits "subtype-selective" activity against one subtype relative to the other. For example, in some embodiments, the anti-progestational agent is active against PR-A while being substantially inactive against PR-B, or vice versa. Subtype-selectivity can be measured as the ratio of $IC_{50}$ value for a target progesterone receptor to the $IC_{50}$ value for a non-target receptor subtype. In some embodiments, a "subtype-selective" anti-progestational agent has a subtype selectivity that is less than about 1:2, and preferably less than about 1:10, and more preferably less than about 1:50, and most preferably less than about 1:100.

In some embodiments, the anti-progestational agent selectively antagonizes PR-B, which is differentially expressed in the endometrial lining (e.g., Wang et al., Mol Hum Reprod., 4(4):407-12 (1998)), relative to PR-A, which prevents side effects associated with secondary activity against non-uterine and/or other untargeted progesterone receptors. In further embodiments, the anti-progestational agent exhibits "target-selective" activity against progesterone receptors relative to non-progesterone receptors. For example, in some embodiments, the anti-progestational agent is substantially inactive or substantially less active against glucocorticoid receptors, estrogen receptors, and/or other steroid receptors. In some embodiments, the anti-progestational agent is a progesterone antagonist that is substantially inactive against glucocorticoid receptors, such as ZK230211 (described, e.g., in Fuhrrmann et al., J Med Chem, 43: 5010-5016 (2000)), Org 31710, Org 31806, Org 33628, and compounds described in Tabata et al., Eur J Pharm, 430: 159-165 (2001), Philibert et al., J Steroid Biochem., 34(1-6): 413-7 (1989), and Pooley et al., J Med Chem, 41: 3461-3466 (1998).

In some embodiments, the subtype and/or target selective activity of an anti-progestational agent is achieved by administering the agent at a dosage and/or in a manner that produces a concentration in the target organ or tissue (e.g., the uterine lining) that is therapeutically effective against one or more targeted progesterone receptors, while being sub-therapeutic at other receptors and/or targets. Advantageously, the subtype-selective activity of an anti-progestational agent results in improved efficacy, fewer side effects, lower effective dosages, less frequent dosing, and/or other beneficial therapeutic properties relative to non-selective agents.

While the anti-progestational agents described herein can be administered as the sole active pharmaceutical agent, they can also be used in combination with one or more additional active agents, such as another anti-progestational agent and/or an agent with a distinct activity. When administered as a combination, the therapeutic agents can be formulated as separate compositions that are administered at the same time or sequentially at different times, or given as a single composition. The invention is not limited in the sequence of administration. In some embodiments, a progesterone receptor modulator has a synergistic effect with the one or more additional active agents. In some embodiments, one or more additional agents potentiate the effect of the progesterone receptor modulator and/or the progesterone receptor modulator potentiates the effect of the additional agent(s). Methods for assessing synergism, potentiation, and other combined pharmacological effects are known in the art, and described, e.g., in Chou and Talalay, Adv Enzyme Regul., 22:27-55 (1984). In some embodiments, combination therapy with an anti-progestational agent and one or more additional agents, or with two or more anti-progestational agents, results in a enhanced efficacy, safety, therapeutic index, and/or tolerability, and/or reduced side effects (frequency, severity, or other aspects), dosage levels, dosage frequency, and/or treatment duration relative to monotherapies with each of the components of the combination.

Information indicating that anti-progestational agents would be effective in a number of medical conditions is available. Non-limiting examples of medical conditions or disorders that could be treatable with the anti-progestational agent methods, dosing regimens and medication of the present invention include: uterine leiomyomata, endometriosis, symptoms associated with ovarian cysts, polycystic ovarian syndrome, breakthrough bleeding, intermittent bleeding, irregular withdrawal bleeding, dysfunctional uterine bleeding, adenomyomas, polymenorrhea, dysmenorrhea, severe dysmenorrhea, menorrhagia, hirsutism, iron deficiency anemia, acne, benign breast disease, fluctuations in infection levels, temporomandibular disorder, catamenial symptoms, non-menstrual related headache, nausea, depression, hypoestrogenism, pelvic inflammatory disease, loss of bone density, cancers, other tumors, male contraception, anti-glucocorticoid effects, and labor and delivery. While these conditions or disorders are described separately in places, it is to be understood that the conditions and disorders described hereinafter in more detail and their respective symptoms and causes can overlap.

Importantly, while a role for anti-progestational agents has been indicated in the treatment of these conditions, the prior art has suggested higher doses of anti-progestational agents that the present invention shows are not necessary. For example, U.S. Pat. No. 6,225,298 to Spicer et al. (issued May 1, 2001) suggests that an appropriate dose of mifepristone could be 10 to 100 mg daily. Eisinger et al., (supra) has shown that 5 mg of mifepristone can be effective at treating uterine leiomyomata when given daily for 6 months. As stated earlier, however, these doses and/or lengths of treatments can be associated with troublesome side effects. Therefore, a need remains for a treatment option that does not cause these effects. The low dose methods, dosing regimens and medications of the present invention provide such options.

The following discussion describes a subset of the number of progesterone-related disorders that can be beneficially treated with the low dose methods, dosing regimens and medications of the present invention.

Uterine leiomyomata. As stated previously, uterine leiomyomata are generally non-malignant tumors that may occur in up to 80% of women over 30 years old. Uterine leiomyomata are benign growths of uterine muscle that sometimes exist singly, but most often are multiple and range in size from microscopic to filling most of the lower abdominal cavity. Many women with uterine leiomyomata have no symptoms at all. For those that do, the most common complaints are pressure symptoms and heavy, prolonged periods leading to iron-deficiency anemia, as well as painful periods (dysmenorrhea which can transition into severe dysmenorrhea). There may be pressure in the pelvic region from the enlarged uterus, and the resulting symptoms are often related to where the uterine leiomyomata are exerting pressure (e.g., increased urinary frequency, constipation or difficulty with bowel movements). The pressure can also cause backache, lower abdominal discomfort, and pain during and after intercourse. The presence of uterine leiomyomata can also cause reproductive problems such as infertility, multiple miscarriages, premature labor, or labor complications. These generally non-malignant tumors are one of the most common reasons for surgery in women during their reproductive years.

Endometriosis. Many women, about 5-10% of those in their reproductive years, are afflicted with endometriosis. The current concept of endometriosis is that the endometrial glands and stroma are shed through Fallopian tubes during menstruation, after which they implant onto the peritoneum, and initiate growth. Initially, the existence of translocated endometrial cells can only be proven microscopically on the peritoneal lining of the pelvis, or even at extra-pelvic sites such as the diaphragm in the upper abdomen. Murphy et al., 46 Fert. and Sterility 522-524 (1986). But the occurrence of regular, menstrual bleeding at those sites over time leads to angiogenesis and growth of visible lesions where none had been visible before, and pain and infertility that develop from the bleeding at, and into those sites. Brosens, supra. Symptoms usually subside during pregnancy and lactation, after castration premenopausally, and as the hypoestrogenemia of the peri-menopause develops. Endometriosis is a life-long, genetically facilitated, pathological condition that may be stimulated at any age by unopposed estrogen therapy to produce recurrent symptoms.

Women with endometriosis can suffer progressive, disabling dysmenorrhea and pelvic pain around the time of menses. Brosens, 176 Am. J. Obstet. Gynecol. 263-7 (1997). Other common symptoms and signs of endometriosis include dyspareunia, pain unrelated to menses, discomfort upon pelvic exam, induration, and cul de sac tenderness. In addition, pelvic pain unassociated with menses may restrict afflicted women to measured participation in athletic and other physical activities, such as dancing and hiking.

The peri-menstrual pain experienced by women afflicted with endometriosis may be relieved in part by non-steroidal anti-inflammatory bioactive agents (NSAID's). But those not benefited adequately require ovulation-suppressing treatments and/or are treated with bioactive agents such as danazol or GnRH analogs that have significant side-effects.

Menstrual Disorders. Menstrual disorders include, but are not limited to polymenorrhea, dysmenorrhea, dysfunctional uterine bleeding, breakthrough bleeding, intermittent bleeding, dysfunctional uterine bleeding, menorrhagia and adenomyoma as well as premenstrual symptoms such as, but not limited to, those associated with premenstrual syndrome (PMS) or Premenstrual Dysphoric Disorder (PMDD).

During the luteal phase of the menstrual cycle, as many as 75% of women with regular menstrual cycles experience some symptoms of premenstrual syndrome (PMS), a recurring, cyclical disorder involving behavioral, emotional, social and physical symptoms. Steiner et al., 48 Annu. Rev. Med. 447-55 (1997). Behavioral, emotional and social symptoms include, but are not limited to, irritability, mood swings, depression, hostility and social withdrawal. Physical symptoms include, but are not limited to, bloating, breast tenderness, myalgia, migraines or headaches, abdominal pain, and fatigue. True PMS only occurs during the luteal phase of the menstrual cycle, with a symptom-free period during the follicular phase. The etiology of PMS is still unknown.

A subgroup of women with PMS, about 5%, exhibit symptoms that are primarily related to a severe mood disorder. In these women, the diagnosis of Premenstrual Dysphoric Disorder (PMDD), as defined in the Fourth edition of the Diagnostic and Statistical Manual of Mental Disorders (DSM-IV), can be applied (see "Premenstrual Dysphoric Disorder," in DSM-IV: Diagnostic and Statistical Manual of Mental Disorders, 4$^{th}$ Ed., American Psychiatric Association, Washington, D.C., pp. 715-718 (1994)). According to the DSM-IV, a woman with PMDD must have at least five premenstrual symptoms during the luteal phase, with at least one of the symptoms being an emotional or "core" symptom. The core symptoms must be irritability, anger, mood swings, tension or depression (and interfere with daily activities), and must be confirmed by a prospective daily rating for at least two cycles. There is also a subgroup of women who experience severe PMS, which accounts for about 20% of the PMS population. These women experience severe emotional symptoms that do not fall under the strict criteria of PMDD as defined in DSM-IV but require medical attention.

Catamenial symptoms. Catamenial symptoms are those associated with conditions, disorders, or diseases that can worsen around the time of menses. Thus, a role for progesterone is indicated. Such conditions, disorders, or diseases include, but are not limited to, asthma, rheumatoid arthritis, migraine headaches, seizure disorders or epilepsy, depression, multiple sclerosis and diabetes. A subset of these conditions and symptoms are described more fully below.

Arthritis is a prevalent chronic condition. Hormonal factors can influence the frequency and severity of arthritis. In some women, arthritis symptoms such as joint stiffness, swelling and pain peak during the postovulatory phase of the menstrual cycle, and cyclic changes in local antibody release, white blood cell subpopulations and altered pain perception have been proposed as possible mechanisms. Case, & Reid, 158 Arch. Intern. Med. 1405-12 (1998). Estrogen administered as a single agent, and as part of a combined oral contraceptive has been reported to benefit some women. Kay & Wingrave, 1 Lancet 1437 (1983); Linos et al., 1 Lancet 1871 (1978).

About 60% of women with migraines report a relationship of their occurrence with menstruation. Case & Reid, supra. Decreasing levels of estrogen during the late luteal phase of the menstrual cycle or abrupt withdrawal of estrogen as during the hormone-free period in women taking oral contraceptives are thought to trigger migraine attacks. Sulak et al., 95 Obstet. Gynecol 261-66 (2000); Kudrow, 15 Headache 36-49 (1975); Whitty et al., 1 Lancet 856-59 (1966).

Catamenial epilepsy refers to seizure disorders that occur or worsen around menstruation. It is believed to result from cyclic alterations in both ovarian hormone levels and bioactive agent metabolism. Case & Reid, supra.

Ovarian cysts and Polycystic Ovarian Syndrome. Ovarian cysts and polycystic ovarian syndrome can cause symptoms including, but not limited to, pelvic pain, dysmenorrhea, abnormal uterine bleeding, acne, and hirsutism. Ovarian cysts arise from functional cysts that commonly occur around midcycle, when a follicle destined to become an egg fails to mature. Instead of leaving the ovary in a process known as ovulation, it remains inside, floating in a tiny sac of fluid. It is that sac that eventually forms into a cyst. Although rarely malignant, ovarian cysts lead to 200,000 hospitalizations in the United States each year. For some women, some studies have shown that the cysts develop cycle after cycle. Though ovarian cysts can sometimes be asymptomatic, they can also cause pain (constant pelvic pain, pain during intercourse, pain during pelvic movement, and/or pain before or after menses), abnormal bleeding (lengthened, shortened, irregular and/or absent menses), and/or abdominal bloating or distension.

Labor and delivery. Anti-progestational agents may be useful for cervical ripening prior to labor induction such as at term or when labor must be induced due to fetal death. Anti-progestational agents may also be used to help induce labor in term or post-term pregnancies.

Antiglucocorticoid effects. While in most cases the antiglucocorticoid effects of anti-progestational agents such as mifepristone are undesirable, they can be beneficial in some patients. For example, anti-progestational agents with anti-glucocorticoid effects, such as mifepristone, can be useful in the treatment of Cushing's syndrome, and could be beneficial in the treatment of immune disorders.

Cancers. Anti-progestational agents may be useful for the treatment of hormone dependent cancers, including breast, uterine and ovarian cancers. See, for example, Horwitz, et al., Horm Cancer, 283 pub: Birkhaeuser, Boston, Mass., ed. Vedeckis. Anti-progestational agents have also been shown to be effective in a model of hormone dependent prostate cancer, which may also indicate their utility in the treatment of this condition in men. Michna, et al., 761 Ann. N.Y. Acad Sci. 224 (1995).

A role for progesterone (and thus anti-progestational agents in treatment) for breast cancer is described more fully. The breast has a tightly regulated pattern of growth primarily under the control of steroid hormones. The effects of steroid hormones on the normal breast are increasingly well understood. Estrogen induces some breast epithelial proliferation, but estrogen and progesterone together produce even greater cell proliferation. Pike et al., 15 Epidemiol. Rev. 17-35 (1993). In non-pregnant premenopausal women, the breast epithelium undergoes repetitive periods of cell proliferation and cell loss secondary to cyclic ovarian activity. In the terminal duct lobular unit (TDLU) of the premenopausal breast, cell proliferation is low during the follicular phase of the menstrual cycle. Following ovulation, progesterone is produced by the corpus luteum and TDLU cell proliferation increases two- to three-fold over follicular levels. Pike et al., supra. Consistent with the breast cell proliferation rates, the size and number of terminal ductules peak during the late-luteal phase. Longacre & Barlow, 10 Am. J. Surg. Path. 382-93 (1986). If fertilization and pregnancy do not ensue, progesterone levels fall, the rate of breast cell division decreases, and a wave of cell death by apoptosis follows the peak in cell proliferation. Anderson et al., 46 Br. J. Cancer 376-82 (1982).

Proliferating cell populations are more susceptible to carcinogenic effects, and the rise in cancer risk associated with cell proliferation is secondary to an increased chance of mutation and loss of tumor suppressor genes. Preston-Martin et al., 50 Cancer Res. 7415-21 (1990). Thus, breast cancer risk would be predicted to increase the greatest during periods of exposure to both estrogen and progesterone, as in the premenopausal period or in women receiving combined oral contraceptives (COCs); less during periods of exposure only to estrogen, as in postmenopausal women receiving estrogen replacement therapy (ERT) or in obese postmenopausal women; and least during periods of exposure to very low levels of both hormones, as in non-obese postmenopausal Asian women.

Anti-progestational agents may also be useful in treating or inhibiting the development of other types of cancer such as meningiomas, non-malignant brain membrane tumors, that, although non-malignant, result in death of the patient.

Male contraception. Anti-progestational agents, whether acting through anti-progestational or anti-glucocorticoid activity can interfere with sperm viability. Thus, the anti-progestational agents of the present invention could provide a mechanism of male contraception.

The foregoing discussion provides a number of medical conditions and/or disorders that could benefit from the low dose anti-progestational agent methods, dosing regimens and medications of the present invention.

In some embodiments, low dose anti-progestational therapies described herein comprise a step of identifying a patient in need of anti-progesterone treatment, and administering to the patient an effective, progesterone receptor-modulating amount of an anti-progestational agent. In various embodiments, identifying a patient in need of anti-progesterone treatment comprises identifying a patient who has or will be exposed to a factor or condition known to enhance the production or effect of progesterone, including but not limited to pregnancy, menstruation, or medications that enhance the amount and/or activity of progesterone (e.g., birth control). In some embodiments, identifying a patient in need of anti-progesterone treatment comprises identifying a patient suffering from one or more symptoms caused or exacerbated by the effects of progesterone, including but not limited to, uterine leiomyomata, arthritis, menstrual disorders (e.g., PMS), pregnancy-related fatigue and/or depression, post-partum depression, and migraines.

In some embodiments, identifying a patient in need of anti-progesterone treatment comprises selecting a population or sub-population of patients, or an individual patient, that is more amenable to treatment and/or less susceptible to side effects than other patients having the same disease or condition. In some embodiments, the patient has been identified as being non-responsive to treatment with primary medications for the condition(s) targeted for treatment, and the anti-progestational agent is administered in a method for enhancing the responsiveness of the patient to a co-existing or pre-existing treatment regimen. In other embodiments, the method or treatment comprises administering a combination of a primary medications, wherein an anti-progestational agent exerts a greater-than-additive effect (e.g., a synergistic effect) with an additional therapeutic agent in treating the disease targeted for treatment. In some embodiments, identifying a patient in need of anti-progesterone treatment comprises detecting one or more genetic markers indicative of being predisposed to a progesterone-related disorder.

The anti-progestational agents of the present invention also can be used, without limitation, in the form of salts derived from pharmaceutically or physiologically acceptable acids or bases. These salts include, but are not limited to, the following salts with inorganic acids such as, without limitation, hydrochloric acid, sulfuric acid, nitric acid, phosphoric acid and, as the case may be, such organic acids as acetic acid, oxalic acid, succinic acid, and maleic acid. Other salts include, without limitation, salts with alkali metals or alkaline earth metals, such as sodium, potassium, calcium or magnesium in the form of esters, carbamates and other conventional "pro-bioactive agent" forms, which, when administered in such form, convert to the active moiety in vivo.

Anti-progestational agents provided herein that contain a chiral center include all possible stereoisomers, including racemic mixtures and compositions comprising varying proportions of each enantiomer, including compositions substantially free of a non-preferred enantiomer or substantially enriched in a preferred enantiomer. Thus, for example, compositions comprising the S enantiomer substantially free of the R enantiomer, or the R enantiomer substantially free of the S enantiomer are contemplated. If a named anti-progestational agents comprises more than one chiral center, the present disclosure includes compositions comprising mixtures of varying proportions of the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s).

In some embodiments, the anti-progestational agents is an antisense nucleotide (e.g., siRNA) that specifically hybridizes with the cellular mRNA and/or genomic DNA corresponding to the gene(s) of a target progesterone receptor, or a molecule that otherwise modulates progesterone receptor activity, so as to inhibit their transcription and/or translation, or a ribozyme that specifically cleaves the mRNA of a target protein. Antisense nucleotides and ribozymes can be delivered directly to cells, or indirectly via an expression vector which produces the nucleotide when transcribed in the cell. Methods for designing and administering antisense oligonucleotides and ribozymes are known in the art.

The medications of the present invention can be administered by any route where they are active. For example, administration can be, without limitation, oral, injectable (without limitation, parenteral, subcutaneous, intravenous, intramuscular, intraperitoneal, or by depot injections), topical, transdermal, intravaginal, intrauterine, sublingual, buccal, rectal, by inhalation, through implants or through ocular routes. Suitable pharmaceutical excipients and formulations for a variety of routes of administration are known in the art and are described, for example, in Remington's Pharmaceutical Sciences (19th ed.) (Genarro, ed. (1995) Mack Publishing Co., Easton, Pa.). One of ordinary skill in the art will readily appreciate how the anti-progestational agents of the present invention can be administered through each of the above administration routes. A description of a subset of these administration routes is nonetheless provided.

In some embodiments, antiprogestational agents described herein are selected, formulated, administered, and/or modified to prevent and/or facilitate passage across one or more biological barriers, including but not limited to the blood brain barrier, the blood-cerebrospinal fluid (CSF) barrier, the intestinal epithelium, the placenta, and/or the mucosal lining. For example, in some embodiments, an anti-progestational agent is permeable across the gut epithelium while being substantially impermeable across the blood-brain barrier, so as to allow oral administration with minimal dose-limiting CNS side effects.

In some embodiments, an anti-progestational agent is selected on the basis of one or more characteristics that correlate with the desired permeability, such as polarity, hydrophobicity/hydrophilicity, size, charge, and affinity for transporters, channel proteins, receptors, and other molecules involved in transport across the barrier of interest. In some embodiments, the anti-progestational agent is conjugated to a carrier that imparts the desired physical properties. For example, a carrier molecule may comprise an internalization domain, such as a peptide sequence recognized by one or more cell-surface receptors, which facilitates the uptake of the drug into cells targeted for treatment via active transport.

Relevant factors and strategies for selecting and designing agents with desired permeability across biological barriers are known in the art, and are described, e.g., in Sharma et al., Pharmazie., 61(6): 495-504 (2006), Borovac et al., J Control Release, 115(3): 266-74 (2006), He et al., Int J Pharm. Epub (Oct. 21, 2006), Majumdar and Mitra, Expert Opin Drug Deliv., 3(4): 511-27 (2006) and Panyam and Labhasetwar, Curr Drug Deliv. 1(3): 235-47 (2004), each of which is hereby incorporated by reference in its entirety. Advantageously, anti-progestational agents administered in methods provided herein are selectively permeable so as to achieve therapeutic levels upon administration in targeted cells, tissues, organs, compartments, etc. at dosing levels, frequencies, and durations that avoid undesirable side effects of standard treatments involving standard preparations of the agent.

In one embodiment of the present invention, the anti-progestational agents of the present invention can be delivered through oral administration routes. For solid orally-administrable compositions, conventional nontoxic solid carriers may be used which include, without limitation, pharmaceutical grades of mannitol, lactose, starch, magnesium stearate, sodium saccharine, talcum, cellulose, glucose, sucrose, magnesium, carbonate, and the like. Specifically, and in one embodiment, oral solid dosage forms can be compressed into tablets or capsules. Compressed tablets may contain any of the excipients described above which can increase the bulk of the anti-progestational agents (and other active ingredients if included) so that production of a compressed tablet of practical size is possible. Binders, which are agents which impart cohesive qualities of powdered materials, also can be used. Non-limiting examples of appropriate binders include starch, gelatin, sugars such as, without limitation, lactose, sucrose, mannitol, sorbitol or dextrose, and natural or synthetic gums. Disintegrants also can be used to create appropriate tablets or capsules. Disintegrants can facilitate breakup of the tablet once ingested. Appropriate non-limiting disintegrants include, without limitation, starches, clays, celluloses, algins, gums and crosslinked polymers, the foregoing more specifically including, without limitation, cross-linked polyvinyl pyrrolidone, agar, or alginic acid or a salt thereof such as sodium alginate. Lubricants and glidants also can be used in the solid oral administration forms of the present invention. These materials serve to reduce adhesion of the dosage form material to surfaces in the manufacturing process and also improve the flow characteristics of the powder material used during manufacture. An appropriate glidant includes, without limitation, colloidal silicon dioxide. Appropriate lubricants include, without limitation, talc and stearic acids. Other commonly-used and appropriate excipients include cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP).

Procedures for the production and manufacture of compressed tablets and capsules are well known by those skilled in the art (See Remington). In one embodiment, the solid oral dosage forms of the present invention can include hard or soft gelatin shells as a container for a particular mixture of anti-progestational agents and other active or inactive ingredients. Procedures for production and manufacture of hard or soft gelatin shells are also well known in the art (See Remington).

Oral dosage forms of the present invention can also come in the form of dragees, capsules, liquids, gels, syrups, slurries, suspensions, or lozenges and the like, all formulated in well-known and conventional manners. When dragees are chosen as a dosage form of the present invention, dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The anti-progestational agents of the present invention can also be administered by injection including, without limitation, parenteral injection, subcutaneous injection, intravenous injection, intramuscular injection, intraperitoneal injection or by depot injection. When administered by injection, the anti-progestational agents of the present invention can be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the anti-progestational agents of the present invention can be in powder form for constitution with a suitable vehicle, e.g., sterile pyrogen-free water, before use. In one embodiment, adjuvants such as, without limitation, local anesthetics, preservatives and buffering agents can also be included in the aqueous solution. To enhance the stability of the anti-progestational agents of the present invention, the composition can be frozen after filling into a vial and the aqueous solution removed under vacuum. The dry lyophilized powder can then be sealed in the vial and an accompanying vial of water for injection can be supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. In one embodiment, a surfactant or wetting agent can be included in the composition to facilitate uniform distribution of the anti-progestational agents of the present invention.

In addition to the formulations just described, the anti-progestational agents of the present invention can also be formulated as depot preparations. Such long acting formulations can be administered by implantation (for example subcutaneously or intramuscularly) or by intramuscular injection. In one embodiment, depot injections can be administered at about 1 week to about 1 month to about 6 month intervals or longer. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In one embodiment, the anti-progestational agents of the present invention can be delivered through topical administration. When topical administration is chosen, the anti-progestational agents of the present invention can be formulated as, without limitation, solutions, gels, ointments, creams, patches, suspensions, and the like, as are well known in the art. In some embodiments, administration can be by means of a transdermal patch. In transdermal administration, the anti-progestational agents of the present invention can be applied to a plaster, or another transdermal, therapeutic system. Regardless of the specific transdermal delivery method chosen, penetration enhancers, including, without limitation, dimethyl sulfoxide, dimethyl acetamide and dimethylformamide can be included.

Implants can also be used to deliver the anti-progestational agents of the present invention. Implants can comprise, without limitation, polymeric devices which slowly release or slowly erode and release within the body to provide appropriate amounts of anti-progestational agents over time. When polymers are used, appropriate polymers include, without limitation, non-toxic hydrogels, silicones, polyethylenes, ethylene-vinyl acetate copolymers and other biodegradable polymers. Hydrogels include, without limitation, polyhydroxyalkyl methacrylates, polyacrylamide and polymethacrylamide, polyvinylpyrrolidone and polyvinyl alcohol. An appropriate silicone includes, without limitation, polydimethylsiloxane. Biodegradable polymers include, without limitation, polylactic acid (PLA), polyglycolic acid (PGA), copolymers of PLA and PGA, and polyamides.

The implants of the present invention can include subcutaneous devices such as those routinely used to deliver norgestrienone or progestin R2323 and other medicaments. Other implants include intravaginal and intrauterine implantable devices. For vaginal administration, vaginal creams, rings and pessaries are also appropriate.

In one embodiment, the present invention can include rectal compositions, such as, without limitation, suppositories or retention enemas containing conventional suppository bases such cocoa butter, polyethylene glycols (carbowaxes), polyethylene sorbitan monostearate, and mixtures of these with other compatible materials to modify the melting point or dissolution rate.

Another embodiment of the present invention can include the administration of anti-progestational agents with or without other added active or inactive ingredients through inhalation. In one embodiment, inhalation can occur through the use of an aerosol spray using, without limitation, pressurized packs or a nebulizer with the use of a suitable propellant such as, without limitation, dichlorodifluoromethane, trichlorofluoromethane, dichlorotetrafluoroethane, carbon dioxide or other appropriate gases. In the case of a pressurized aerosol, dosage amounts can be controlled by providing a valve to deliver a metered amount. Capsules and cartridges of, for example, gelatin for use in an inhaler or insufflator can be formulated containing a powder mix of active ingredients and a suitable powder base such, without limitation, lactose or starch.

As should be understood by the previous description of administration routes, formulations of the present invention can include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and dosage forms which include, but are not limited to, solutions, suspensions, emulsions, and dry powder; comprising an effective amount of anti-progestational agents as taught by this invention. The anti-progestational agents of the present invention can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modem Pharmaceutics", Banker & Rhodes, Marcel Dekker, Inc. 1979; and "Goodman & Gilman's The Pharmaceutical Basis of Therapeutics," 6th Edition, MacMillan Publishing Co., New York 1980 can be consulted.

The dosage forms described may also be provided in sustained-release forms. As is understood by one of ordinary skill in the art, a chosen dosage form can be provided in a sustained release form by, without limitation, increasing the particle size of the drug, embedding the drug in a matrix, coating the drug or dosage form containing the drug and/or forming complexes of the drug with materials such as ion-exchange resins. Materials that can be suitable for producing sustained-release coatings on oral dosage forms include, without limitation, mixtures of waxes (beeswax, camauba wax, etc. with, without limitation, glyceryl monostearate, stearic acid, palmitic acid, glyceryl monopalmitate and cetyl alcohol; shellac and zein; ethylcellulose; acrylic resins, cellulose acetate (including, without limitation, diacetate and triacetate); and silicone elastomers.

As stated previously, the anti-progestational agents of the present invention can be administered in combination or concurrently with other active ingredients. For example, in one embodiment the anti-progestational agents of the present invention can be administered with another treatment that has been found to be useful in treating uterine-related disorders. In another embodiment, the anti-progestational agents of the present invention can be administered with another treatment that has been found to be useful in treating catamenial symptoms. Non-limiting examples of these types of other treatments include GnRH agonists, such as, without limitation, Lupron®, Synarel® or Zolodex®, danazol or GnRH analogs, birth control pills, depo-provera acetate, myomectomy, uterine artery embolization, endometrial ablation, guided ultrasound therapy, cortisol or synthetic cortisol-like bioactive agents, or levonorgestrel or similar agents. The anti-progestational agents can also be administered after a treatment such as GnRH agonists, such as, without limitation, Lupron®, Synarel® or Zolodex®, danazol or GnRH analogs, birth control pills, depo-provera acetate, myomectomy, uterine artery embolization, endometrial ablation, guided ultrasound therapy, cortisol or synthetic cortisol-like bioactive agents, or levonorgestrel or similar agents has concluded and the treatment was determined to provide inadequate relief from the condition or disorder at issue. The anti-progestational agents can also be administered before a treatment including GnRH agonists, such as, without limitation, Lupron®, Synarel® or Zolodex®, danazol or GnRH analogs, birth control pills, depo-provera acetate, hysterectomy, myomectomy, uterine artery embolization, endometrial ablation, guided ultrasound therapy, cortisol or synthetic cortisol-like bioactive agents, or levonorgestrel or similar agents. Administering the anti-progestational agents of the present invention at the doses described can be especially beneficial as a way to shrink uterine leiomyomata before a surgical treatment such as, without limitation, hysterectomy, myomectomy, uterine artery embolization and endometrial ablation.

The anti-progestational agents of the present invention can also be administered with other active ingredients. For example, in one embodiment the anti-progestational agents of the present invention could be administered with vitamin D and/or calcium to aid in the maintenance or prevention of bone density loss. The form of vitamin D and of calcium used in the present invention would be well known to those of skill in the art, as would the amount. For example, calcium can be administered in the form of calcium carbonate, at a daily dosage level of 500 mg.

When the anti-progestational agents of the present invention are administered alone (either as a first treatment or following a previous treatment with another bioactive agent or following a procedure), the agents can be delivered between about 1 and about 12 times daily, between about 1 and about 84 times weekly, between about 1 and about 372 times monthly or between about 1 and about 4,464 times yearly. When administered concurrently within another type of medication, the two agents can be administered together in one dosage form (manufactured and by administration routes described above) or can be administered in separate dosage forms. When administered in separate dosage forms, the dosage forms can be the same or can be different dosage forms. The anti-progestational agents of the present invention can also be administered concurrently with three or more additional medication types or other treatment procedures. Concurrently administered medications and/or other treatment procedures can also be administered between about 1 and about 12 times daily, between about 1 and about 84 times weekly, between about 1 and about 372 times monthly or between about 1 and about 4,464 times yearly.

Following the administration of an anti-progestational agent of the present invention for a period of time, a patient can receive a maintenance dose of the same or a different anti-progestational agents of the present invention. The maintenance doses will generally cause a blood level of the anti-progestational agents that is generally lower than that observed during its administration during the first period of time. Again, the maintenance dose could be administered between about 1 and about 12 times daily, between about 1 and about 84 times weekly, between about 1 and about 372 times monthly or between about 1 and about 4,464 times yearly. As will be understood by one of skill in the art, the dosing schedule chosen will dictate the dosage used at each administration time.

The anti-progestational agents of the present invention can be administered in dosage amounts of about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

In further embodiments, anti-progestational agents of the present invention can be administered in dosage amounts of less than about 4.75 mg, less than about 4.5 mg, less than about 4.25 mg, less than about 4.0 mg, less than about 3.75 mg, less than about 3.5 mg, less than about 3.25 mg, less than about 3.0 mg, less than about 2.75 mg, less than about 2.5 mg, less than about 2.25 mg, less than about 2.0 mg, less than about 1.75 mg, less than about 1.50 mg, less than about 1.25 mg, less than about 1.0 mg, less than about 0.75 mg, less than about 0.5 mg, or less than about 0.25 mg, or less than about 0.75 mg.

Whether administering a first round of anti-progestational agent treatment or a maintenance dose round of such treatment, the administration of these agents can occur, without limitation, for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 1 year, about 1 year plus any of the weekly increments described above, about 2 years plus any of the weekly described above or more. When from 4.75 mg to about 5.5 mg is chosen as a dose, administration will not exceed 4 weeks. When from about 0.1 mg to about 0.2 mg is chosen as a dose, administration can be limited to a patient weighing less than 110 pounds, although such a limitation is not required.

In further embodiments, antiprogestational agents described herein are administered for a duration of less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, or less than about 1 week.

The anti-progestational agents of the present invention can be produced in the form of a kit or package, with dosages arranged for proper administration. For example, in embodiments adopting solid oral dosage forms, a kit can contain a pharmaceutical package including the oral dosage form in bottles or blister packs. If a particular kit includes a treatment regimen including concurrent administration of the anti-progestational agents of the present invention with another treatment or the use of the anti-progestational agents of the present invention following another treatment or the use of the anti-progestational agents of the present invention followed by a maintenance dose, all required dosages and medications can be contained in one kit. The kit can contain these combination-type dosages in a synchronized or fixed sequence manner wherein the sequence or arrangement of the dosage units is explained by instructional information found with or within the kit (see below). Thus, for example, a kit of the present invention could include 180 tablets containing 2.5 mg mifepristone and 180 tablets containing 1.0 mg mifepristone. In this example, the instructional information could provide that a 2.5 mg tablet be taken daily for about 6 months. At the completion of this six months, a 1.0 mg tablet should be taken daily for another about 6 months as a maintenance dose. While this example describes one appropriate kit of the present invention, it should not be read to limit the possible combinations of administrations possible with the kits of the present invention.

The kits of the present invention can also include injectable forms of the anti-progestational agents of the present invention. In one embodiment, a kit of the present invention can contain one or more of the following in a package or container: (1) one or more anti-progestational agents of the present invention; (2) one or more pharmaceutically acceptable adjuvant or excipient; (3) one or more vehicles for administration, such as one or more syringes; (4) one or more additional bioactive agents for concurrent or sequential administration; and (5) instructions for administration. Embodiments in which two or more of components (1)-(5) are found in the same container are also contemplated.

When a kit is supplied, the different components of the composition may be packaged in separate containers and admixed immediately before use. Such packaging of the components separately may permit long-term storage without losing the active components' functions. When more than one bioactive agent is included in a particular kit, the bioactive agents may be (1) packaged separately and admixed separately with appropriate (similar or different) vehicles immediately before use, (2) packaged together and admixed together immediately before use or (3) packaged separately and admixed together immediately before use. If the chosen compounds will remain stable after admixture, however, the admixture need not occur immediately before use but can occur at a time before use, including in one example, minutes, hours, days, months or years before use or in another embodiment at the time of manufacture.

The reagents included in particular kits of the present invention can be supplied in containers of any sort such that the life of the different components are preserved and are not adsorbed or altered by the materials of the container. For example, sealed glass ampules may contain lyophilized anti-progestational agents or variants or derivatives of thereof or other bioactive agents, or buffers that have been packaged under a neutral, non-reacting gas, such as, without limitation, nitrogen. Ampules may consist of any suitable material, such as, without limitation, glass, organic polymers, such as, polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include, without limitation, test tubes, vials, flasks, bottles, syringes, or the like. Containers may have one or more sterile access ports, such as a bottle having a stopper that can be pierced by a hypodermic injection needle. Other containers may have two compartments that are separated by a readily removable membrane that upon removal permits the components to be mixed. Removable membranes may be, without limitation, glass, plastic, rubber, etc.

As stated earlier, kits can also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

As should be understood, the exact formulation, route of administration, and dosage should generally be determined by the attending physician in view of the patient's condition. Dosage amount and interval can be adjusted individually to provide plasma levels of the active antiprogestational agent which is sufficient to maintain therapeutic effect. Generally, the desired anti-progestational agent is administered in an admixture with a pharmaceutical carrier selected with regard to the intended route of administration and standard pharmaceutical practice.

In some embodiments, an effective, therapeutic amount of an antiprogestational agent described herein is an amount that achieves a concentration of the agent within the target tissue, using the particular mode of administration, at or above the $IC_{50}$ (concentration sufficient for half-maximal inhibition) for activity of the agent at progesterone receptors. In some embodiments, the antiprogestational agent is administered in a manner and dosage that gives a peak concentration of about 1, 1.5, 2, 2.5, 5, 10, 20 or more times the $IC_{50}$ concentration. Methods for determining the concentration of a free compound in plasma and extracellular fluids in the CNS, as well pharmacokinetic properties, are known in the art, and are described, e.g., in de Lange et al., AAPS Journal, 7(3): 532-543 (2005). In some embodiments, an effective amount of an antiprogestational agent described herein is a dose that that produces a concentration of the agent in an organ, tissue, cell, and/or other region of interest that includes the $ED_{50}$ (the pharmacologically effective dose in 50% of subjects) with little or no toxicity.

In some embodiments of the methods described herein, administering a low dose of an anti-progestational agent allows effective treatment of a condition targeted for treatment with substantially fewer and/or less severe side effects compared to existing treatment regimens. In some embodiments, combination therapy with an anti-progestational agent and one or more additional agents allows the anti-progestational age and/or the one or more additional agents to be administered at dosages that would be sub-therapeutic when administered individually. In some embodiments, methods described herein allow treatment of certain conditions for which treatment with the same or similar compounds is ineffective using known methods due, for example, to dose-limiting side effects, toxicity, and/or other factors.

In a particular embodiment of the present invention, a business method relating to providing a dosing regimen of an anti-progestational agent and sale of the dosed anti-progestational agent may also be implemented.

In a specific embodiment of the business methods of the present invention, the method can, but need not be, implemented through computer systems. For example, a user (e.g., a health practitioner such as a physician or a pharmacist) may access computer systems via a computer terminal and through the Internet or other means. The connection between the user and the computer system is preferably secure.

In practice, the user may input, for example, information relating to a patient such as the patient's disease state and other factors relating to the patient's treatment. The computer system may then, through the use of the resident computer programs, provide one or more appropriate anti-progestational agent dosing regimens for the patient. The computer program, via the user interface, may also provide pricing and cost comparisons for different anti-progestational agents, in conjunction with, or separate from, appropriate dosing regimens for those anti-progestational agents.

A computer system in accordance with one embodiment of the present invention may be, for example, an enhanced IBM AS/400 mid-range computer system. However, those skilled in the art will appreciate that the methods and apparatus of the present invention apply equally to any computer system, regardless of whether the computer system is a complicated multi-user computing apparatus or a single user device such as a personal computer or workstation. The described computer systems suitably comprise a processor, main memory, a memory controller, an auxiliary storage interface, and a terminal interface, all of which are interconnected via a system bus. Note that various modifications, additions, or deletions may be made to the computer system within the scope of the present invention such as the addition of cache memory or other peripheral devices.

The processor performs computation and control functions of the computer system, and comprises a suitable central processing unit (CPU). The processor may comprise a single integrated circuit, such as a microprocessor, or may comprise any suitable number of integrated circuit devices and/or circuit boards working in cooperation to accomplish the functions of a processor. The processor suitably executes the PK/PD modeling computer programs of the present invention within its main memory.

In one embodiment, the auxiliary storage interface allows the computer system to store and retrieve information from auxiliary storage devices, such as magnetic disks (e.g., hard disks or floppy diskettes) or optical storage devices (e.g., CD-ROM). One suitable storage device is a direct access storage device (DASD). A DASD may be a floppy disk drive which may read programs and data from a floppy disk. It is important to note that while the present invention has been (and will continue to be) described in the context of a fully functional computer system, those skilled in the art will appreciate that the mechanisms of the present invention are capable of being distributed as a program product in a variety of forms, and that the present invention applies equally regardless of the particular type of signal bearing media to actually carry out the distribution. Examples of signal bearing media include: recordable type media such as floppy disks and CD ROMS, and transmission type media such as digital and analog communication links, including wireless communication links.

The computer systems of the present invention may also comprise a memory controller, through use of a separate processor, which is responsible for moving requested information from the main memory and/or through the auxiliary storage interface to the main processor. While for the purposes of explanation, the memory controller is described as a separate entity, those skilled in the art understand that, in practice, portions of the function provided by the memory controller may actually reside in the circuitry associated with the main processor, main memory, and/or the auxiliary storage interface.

Furthermore, the computer systems of the present invention may comprise a terminal interface that allows system administrators and computer programmers to communicate with the computer system, normally through programmable workstations. It should be understood that the present invention applies equally to computer systems having multiple processors and multiple system buses. Similarly, although the system bus of the preferred embodiment is a typical hardwired, multidrop bus, any connection means that supports bidirectional communication in a computer-related environment could be used.

The main memory of the computer systems of the present invention suitably contains one or more computer programs relating to anti-progestational agent administration and an operating system. Computer program in memory is used in its broadest sense, and includes any and all forms of computer programs, including source code, intermediate code, machine code, and any other representation of a computer program. The term "memory" as used herein refers to any storage location in the virtual memory space of the system. It should be understood that portions of the computer program and operating system may be loaded into an instruction cache for the main processor to execute, while other files may well be stored on magnetic or optical disk storage devices. In addition, it is to be understood that the main memory may comprise disparate memory locations.

The following Examples are provided as illustrative embodiments of the present invention. It should be understood that the methods, dosing regimens and medications of the present invention are not limited by the following examples. The teachings of the Examples that follow can be used by those of ordinary skill in the art as guidance in making other, obvious variations that result in similar results as disclosed here.

Embodiments of the present invention can also expressly exclude particular anti-progestational agents, conditions for treatment and/or dosage amounts. For example, certain embodiments of the present invention can exclude mifepristone as an anti-progestational agent. Other embodiments can exclude one or more of onapristone, lilopristone, ZK 112.993, Org 31710, Org 33628, Org 31806, CDB-2914, CDB-4124, RJW, asoprisnil, J900, J956, J912 and J1042.

Certain embodiments of the present invention can also exclude particular conditions for treatment. For example, certain embodiments can exclude the treatment of uterine leiomyomata. Other embodiments can exclude one or more of premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer or for its use in male contraception, anti-glucocorticoid effects or labor and delivery.

Certain embodiments of the present invention can also exclude particular dosages. For example, embodiments of the present invention can exclude one or more of the dosages selected from about 0.1 mg, about 0.15 mg, 0.25 mg, about 0.5 mg, about 0.75 mg, about 1.0 mg, about 1.25 mg, about 1.50 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, about 5.0 mg, about 5.25 mg, about 5.5 mg, about 5.75 mg, about 6.0 mg, about 6.25 mg, about 6.5 mg, about 6.75 mg, about 7.0 mg, about 7.25 mg, about 7.5 mg, about 7.75 mg, about 8.0 mg, about 8.25 mg, about 8.5 mg, about 8.75 mg, about 9.0 mg, about 9.25 mg, about 9.5 mg, about 9.75 mg, about 10.0 mg, about 10.25 mg, about 10.5 mg, about 10.75 mg, about 11.0 mg, about 11.25 mg, about 11.5 mg, about 11.75 mg, about 12.0 mg, about 12.25 mg, about 12.5 mg, about 12.75 mg, about 13.0 mg, about 13.25 mg, about 13.5 mg, about 13.75 mg, about 14.0 mg, about 14.25 mg, about 14.5 mg, about 14.75 mg, about 15.0 mg, about 15.25 mg, about 15.5 mg, about 15.75 mg, about 16.0 mg, about 16.25 mg, about 16.5 mg, about 16.75 mg, about 17.0 mg, about 17.25 mg, about 17.5 mg, about 17.75 mg, about 18.0 mg, about 18.25 mg, about 18.5 mg, about 18.75 mg, about 19.0 mg, about 19.25 mg, about 19.5 mg, about 19.75 mg, about 20.0 mg, about 20.25 mg, about 20.5 mg, about 20.75 mg, about 21.0 mg, about 21.25 mg, about 21.5 mg, about 21.75 mg, about 22.0 mg, about 22.25 mg, about 22.5 mg, about 22.75 mg, about 23.0 mg, about 23.25 mg, about 23.5 mg, about 23.75 mg, about 24.0 mg, about 24.25 mg, about 24.5 mg, about 24.75 mg, about 25.0 mg, about 25.25 mg, about 25.5 mg and about 25.75 mg.

Embodiments of the present invention can also exclude particular administration routes or dosage forms. For example, embodiments of the present invention can exclude one or more of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration and/or one or more of tablets, capsules, cachets, dragees, pills, pellets, granules, powders, solutions, emulsions, fluid emulsions, suspensions, fluid suspensions, semi-solids, ointments, pastes, creams, gels, jellies, foams, implants, patches and sprays.

Embodiments of the present invention can also exclude any combination of anti-progestational agents, conditions, dosages, administration routes and/or dosage forms.

EXAMPLES

Example 1

2.5 mg Mifepristone for the Treatment of Gynecological Disorders

A clinical study of the effectiveness of low doses of mifepristone, specifically 2.5 mg, for the treatment of uterine leiomyomata was conducted. The study was conducted at a single site in Rochester, N.Y.

Subjects: Inclusion criteria for the study included that subjects be (i) female; (ii) 18 years of age to premenopausal; and (iii) willing and able to give informed consent and comply with study requirements; and have (i) at least moderate symptoms of menorrhagia and/or pelvic pain/pressure; (ii) a total uterine volume greater than or equal to 160 cubic centimeters (cc) by ultrasound measurement; (iii) at least one leiomyomata $\geq$2.5 cm in size; (iv) a score of equal to or greater than 39 on the Uterine Fibroid Symptom and Quality of Life Scale; (v) declined standard treatment options for symptomatic leiomyomata; and (vi) agreed to use a barrier method (condoms, diaphragms) or other effective non-hormonal method of contraception (abstinence, sterilization) throughout participation in the study.

Exclusion criteria for the study included: (i) current or planned pregnancy during the study period; (ii) menopausal, as indicated by follicle-stimulating hormone (FSH) level of the reference laboratory; (iii) currently breast-feeding; (iv) untreated abnormal pap smear; (v) presence of conditions other than leiomyomata contributing to pain and/or bleeding; (vi) hemoglobin <9.0 mg/dl; (vii) presence of adnexal masses or tenderness requiring further evaluation or surgery; (viii) grade III or IV hydronephrosis by ultrasound; (ix) severe, active mental disorder; (x) presence of any contraindication to mifepristone including adrenal insufficiency by history, sickle cell disease, active liver disease (liver function tests greater than 1.5 times upper range of normal), severe respiratory disease (PO2 saturation <92%), renal disease (serum creatinine >1.5 mg/dl), major blood clotting defect (significantly abnormal PT and PTT) and/or thromboembolic disease (history of deep vein thrombosis or pulmonary embolus); (xi) current or recent (within the last three months) use of oral systemic corticosteroids, hormones (including estrogens, progestins, oral contraceptives), danazol, anticoagulants, or herbal or botanical supplements with possible hormonal effects; (xii) use within the past six months of GnRH analogs or Depo-Provera®; and (xiii) current or planned use during the study of any of the following medications or products: ketoconazole, itraconazole, erythromycin, grapefruit juice, rifampin, St. John's Wort, phenytoin, phenobarbital or carbamazepine Primary recruitment of subjects occurred through direct advertising and physician referrals. Women who were successfully prescreened were contacted by telephone and invited to an screening session/orientation. Prospective subjects were provided with a verbal and written description of the study and requirements for participation. Written informed consent was obtained from each participant at the screening session/orientation, and medical record releases were obtained and reviewed by the project gynecologist. Participants who gave consent were assigned a study ID number and asked to proceed further with the screening session. A total of fifteen subjects enrolled in this 2.5 mg mifepristone study. During the screening session the following information was collected:

Demographics: Name, address, phone number, primary physician and/or gynecologist, date of birth, race, ethnicity, occupation and years of completed education.

Medical history: Current and past medical conditions, medications and supplements, hospitalizations, surgery, allergies, tobacco, alcohol and illicit drug use.

Gynecologic history: Age of menarche, menstrual history, gynecologic and obstetrical history, and questionnaires for disease-specific and global health-related quality of life (HRQOL), bleeding and pain.

Physical Examination: Height, weight, blood pressure, pulse readings, examination of the breasts, heart, lungs, abdomen, and complete gynecologic examination including bi-manual at screening session/orientation (baseline). Height, weight, blood pressure, pulse readings and examination of the breasts.

Pathology: All subjects underwent endometrial sampling.

Blood samples: Negative pregnancy test and normal liver function testing (ALT, AST), hemoglobin and FSH levels.

Ultrasonography: All subjects underwent abdominal and vaginal ultrasonography and uterine artery and leiomyomata blood flow assessment.

Specifically, uterine leiomyomata size was assessed by transabdominal and/or transvaginal sonography by a single, certified and experienced ultrasonographer. Combined abdominal and vaginal ultrasonography was the standard for assessing leiomyomata size. Ultrasonography has been shown to be a reliable indicator of size when compared to post-operative pathologic findings, (Levi et al., 55 Acta. Obstet. Gynecol. Scand. 261-66 (1976); Fedele et al., 77 Obstet. Gynecol. 745-48 (1991)) and magnetic imaging (Dueholm et al., 186 Am. J. Obstet. Gynecol. 409-15 (2002)) and has been the standard for study of uterine leiomyomata Borgfeldt et al., 79 Acta. Obstet. Gynecol. Scand. 202-07 (2002); Verspyck et al., 89 Eur. J. Obstet. Gynecol. Reprod.

Biol. 7-13 (2000); Nakayama et al., 13 Gynecol. Endocrinol. 382-89 (1999); Fedele et al., 88 Eur. J. Obstet. Gynecol. Reprod. Biol. 91-4 (2000); Weeks et al., 180 Am. J. Obstet. Gynecol. t-13 (1999); Zullo et al., 5 J. Am. Assoc. Gynecol. Laparoscop. 361-66 (1998); de Aloysio et al., 29 Maturitas 261-64 (1998); Zullo et al., 178 Am. J. Obstet. Gynecol. 108-12 (1998); Scialli et al., 64 Fertil. Steril. 313-20 (1995); and Lumsden et al., 101 Br. J. Obstet. Gynaecol. 438-42 (1994). The uterus was measured in three planes and a total volume was calculated. The three largest leiomyomata were evaluated and a volume calculated for each. Endometrial thickness was measured whenever possible in the true sagittal plane. Adnexa including ovaries were assessed in three planes, the volume calculated and abnormal morphology documented. A limited examination of the kidneys was performed to rule out hydronephrosis. Digital images were stored on a disc.

At the beginning of this study, all five subjects had bleeding to start with a mean bleeding period of 25 days. The mean uterine volume was 795 cc with a mean leiomyomata volume (aggregated) of 187.

After the screening session, mifepristone was provided to subjects in 2.5 mg capsules at three-month intervals. (Athenium Laboratories, the supplier of Mifeprex® for Danco Laboratories provided the mifepristone in powder form. From this powder form, gelatin capsules were produced by the project pharmacist with a dosage error range of +/−3% (0.3 mg). "Investigational study med" was printed on the labels and all medication containers were labeled with the FDA IND number, subject name, and address). Subjects were asked to complete a monthly checklist indicating the prevalence and subjective severity of symptoms that may be associated with treatment with 2.5 mg mifepristone. Severity of vaginal bleeding was also assessed by the subjects each day throughout the course of the study using a pictorial chart. This assessment of menstrual bleeding has been previously validated. Janssen et al., 85 Obstet. Gynecol. 977-82 (1995); Higham et al., 97 Br. J. Obstet. Gynecol. 734-39 (1990).

In-person assessments of subjects were taken again after three months of treatment with 2.5 mg mifepristone in order to take additional physical measurements and administer questionnaires for comparison with screening session values.

Following three months of daily administration of 2.5 mg mifepristone, all subjects became amenorrheic. Uterine and leiomyomata volume became 653 and 139 respectively. These numbers represent a mean decrease of 19% and 26% each. Leiomyomata shrinkage ranged from 17% to 48%. All five subjects also increased their mean hemoglobin by one point from 11 mg/dl to 12 mg/dl.

Example 2

5.0 mg Mifepristone for the Treatment of Gynecological Disorders

A study of the effectiveness of 5.0 mg mifepristone in the treatment of gynecological disorders will be carried out in a manner that is similar in all material respects to the 2.5 mg study except that the subjects will be given 5.0 mg mifepristone or placebo for one month. A total of about 40 subjects will be enrolled in the study with about 20 receiving daily 5.0 mg mifepristone and about 20 receiving placebo. When compared to placebo controls, after one month of 5.0 mg mifepristone administration, treated subjects will show, on average, a decrease in blood loss, uterine volume and uterine leiomyomata size, improvements in Quality of Life Scores, and improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures and subjects receiving placebo.

Example 3

1.0 mg Mifepristone for the Treatment of Gynecological Disorders

A clinical study of the effectiveness of a lower dose of mifepristone for the treatment of uterine leiomyomata will be conducted. The methods will be carried out in a manner that is similar in all material respects to those described in Example 1 except that the subjects will be given 1.0 mg mifepristone or placebo for six months.

A total of about forty subjects will enrolled in the 1.0 mg study. At the beginning of the study, all forty subjects will have periods of extended bleeding, with larger than average uterine volumes and mean leiomyomata volumes. About twenty subjects will be given 1.0 mg mifepristone to be taken daily. The remaining subjects will be given a placebo medication to be taken daily.

Following three months of daily administration of 1.0 mg mifepristone, on average, treated subjects will show a decrease in blood loss, uterine volume and uterine leiomyomata size, improvements in Quality of Life Scores, and improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures and subjects receiving placebo.

Following six months of daily administration of 1.0 mg mifepristone, symptoms will continue to improve in treated subjects. More treated subjects will show a decrease in blood loss, uterine volume and uterine leiomyomata size and improvements in Quality of Life Scores. Further improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures and placebo controls will continue to be seen. The study will thus demonstrate the effectiveness of 1.0 mg daily administration of mifepristone in treating uterine leiomyomata.

As described previously, a number of other benign gynecological disorders share symptoms and underlying causes with uterine leiomyomata. For example, progesterone has been implicated in a wide variety of medical conditions and disorders. Therefore, the doses of mifepristone described herein likely will have similar beneficial effects in the treatment of these common disorders including, without limitation, premenstrual syndrome, premenstrual dysphoric disorder, dysfunctional uterine bleeding, polycystic ovarian syndrome, adenomyomas, polymenorrhea, dysmenorrhea, severe dysmenorrhea, menorrhagia, breakthrough bleeding, intermittent bleeding, endometriosis, ovarian cysts, irregular withdrawal bleeding, hirsutism, iron deficiency anemia, acne, benign breast disease, catamenial symptoms, pelvic inflammatory disease, loss of bone density, endometriosis, breast cancer, ovarian cancer, uterine cancer and prostate cancer and for its use in male contraception, anti-glucocorticoid effects or labor and delivery.

Example 4

Long-Term Comparison of Lupron®, 2.5 mg or 5.0 mg Mifepristone for the Treatment of Gynecological Disorders A randomized long term study examining the effectiveness of Lupron®, 2.5 mg and 5.0 mg mifepristone will be undertaken. The methods will be carried out in a manner that is similar in all material respects to those described in Example 1 except that subjects will be 2.5 mg mifepristone daily for one year, 5.0 mg mifepristone daily for one year or will be given monthly intramuscular injections of Lupron Depot® (7.5 mg). A total of about 50 subjects will be included in each treatment group. Measures will be obtained at the screening session as described in Example 1 and after one year of treatment with three month and six month follow up measurements after all therapy has been discontinued.

The results of this study will show that administration of Lupron Depot® (7.5 mg), 2.5 mg mifepristone and 5.0 mg mifepristone all improve symptoms associated with gynecological disorders. Specifically, and on average, subjects will show a decrease in blood loss, uterine volume and uterine leiomyomata size, improvements in Quality of Life Scores, and improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures. At the three month and six month follow up time points, subjects who had received either 2.5 mg or 5.0 mg mifepristone or Lupron Depot® (7.5 mg) continue to show improvements, on average, over baseline in the previously described symptoms. The positive effects of 2.5 mg or 5.0 mg continue at a greater degree and/or for a longer period of time than the positive effects observed with Lupron Depot® (7.5 mg).

Example 5

Effect of 2.5 mg and 5.0 mg Mifepristone on Estradiol Production, Cortisol Production and Adrenal Reserve About 90 subjects meeting the inclusion and exclusion criteria of Example 1 will be recruited with about 10 subjects included in each group to be described. Groups 1 and 2 will be given daily placebo for six months. In Group 1, the effect of placebo on estradiol and cortisol production will be evaluated. In group 2 the effect of placebo on adrenal reserve will be evaluated. Groups 3 and 4 will be given daily 2.5 mg mifepristone for 6 months. In Group 3, the effect of 2.5 mg mifepristone on estradiol and cortisol production will be evaluated. In group 4 the effect of 2.5 mg mifepristone on adrenal reserve will be evaluated. Groups 5 and 6 will be given daily 5.0 mg mifepristone for 6 months. In Group 5, the effect of 5.0 mg mifepristone on estradiol and cortisol production will be evaluated. In group 6 the effect of 5.0 mg mifepristone on adrenal reserve will be evaluated.

Blood samples will be taken from the subjects at a screening session and then once a month for the six month duration of the study. Hormone levels will be measured according to methods well known to those of skill in the art. Specifically, for subjects in Groups 1, 3 and 5, estradiol and cortisol production will be measured using commercially available kits. For example, estradiol will be measured using the Macromolecular Structure Database (MSD®) 17β estradiol assay according to the manufacturer's instructions. Serum cortisol will be measured by RIA using a commercially available kit from ICN Biomedicals, Inc. (Costa Mesa, Calif.) according to the manufacturer's instructions. The results of this portion of the study will show that estradiol and cortisol levels of subjects given 2.5 mg or 5.0 mg mifepristone do not statistically differ from those receiving placebo at any time point tested.

For subjects in Groups 2, 4 and 6, adrenal reserve will be measured using an ACTH stimulation test. Specifically, subjects will be stimulated with 250 μg ACTH intravenously as a bolus injection after an overnight fast. Blood samples will be drawn at 0, 30 and 60 minutes after this ACTH stimulation. Serum cortisol levels will again be measured by ICN Biomedical's commercially available RIA kit according to the manufacturer's instructions. Peak serum cortisol levels of 550 nmol/L or greater will be considered a normal response. The results of this portion of the study show that the cortisol response in response to ACTH stimulation of subjects given either dose of mifepristone does not statistically differ from those receiving placebo at any time point tested, and with the exception of potential outliers in all groups, all subjects show peak serum cortisol levels of at least 550 nmol/L.

Example 6

Long-Term Study of 2.5 mg Mifepristone for the Treatment of Gynecological Disorders A long-term study evaluating 2.5 mg mifepristone in the treatment of gynecological disorders will be undertaken. Again, the methods will be carried out in a manner that is similar in all material respects to those described in Example 1 except that administration of 2.5 mg mifepristone will continue for two years. About 350 subjects will be enrolled in the study. Measures will be taken at the screening session and every four months thereafter for 10 years. Thus, the study will address over time the effectiveness of 2.5 mg mifepristone during the two years of treatment and thereafter for an additional eight years. Mifepristone treatment will begin about 1 week following the screening session with baseline cortisol measures taken at the screening session and subjects coming in a week later for an ACTH stimulation baseline measure. Mifepristone administration will begin the day following each subject's ACTH stimulation baseline measure. Long-term observational reports on fibroid reduction, maintenance of fibroid reduction, recurrent bleeding associated with different endometrial states, data regarding HRQOL, bleeding and pain will be compiled as described in Example 1. Uterine leiomyomata size will be measured once a year. Additionally, on one visit per year, basal cortisol levels will be measured as described in Example 5. On the second visit per year, adrenal reserve will be measured, as described in Example 5. At the end of the treatment period, subjects will be monitored for normal menstrual function.

This study will demonstrate the effectiveness of 2.5 mg mifepristone as a long-term therapy for the treatment of gynecological disorders as well as the lack of adverse side effects associated with this treatment. Specifically, subjects treated with mifepristone will show, on average, a decrease in blood loss, uterine volume and uterine leiomyomata size, improvements in Quality of Life Scores, and improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures. Improvements will remain after treatment with mifepristone is discontinued and for at least a subset of subjects, symptoms will not return to baseline levels throughout the duration of the follow up period. Regarding adrenal function, subjects will not significantly statistically differ from baseline measures in basal cortisol levels or after stimulation with ACTH and normal menstrual function will begin after treatment ends.

Example 7

Effect of Long-Term 2.5 mg Mifepristone Therapy on Endometrial Thickening as Measured by Electron Microscopy A study evaluating the effect of long-term daily 2.5 mg mifepristone administration on endometrial thickening will be undertaken. The methods described in Example 1 will be used to recruit and enroll about 20 subjects into the study.

Before mifepristone treatment begins, biopsies from the endometrial cavity will be obtained using a curette. Biopsies will be taken on day 2 of the menstrual cycle with daily mifepristone treatment starting thereafter. Further biopsies will be taken and analyzed as described below about every 6 months after treatment with mifepristone begins (always on day 2 of the menstrual cycle) for 5 years of treatment.

Biopsied tissues will be processed in a standardized manner as described in Dockery et al., 11 Hum. Reprod. 2251-2256 (1996) and Dockery et al., 3 Hum. Reprod. 715-20 (1988b) which are incorporated by reference herein for their descriptions of tissue processing and related techniques. Specifically, sections will be cut on Epcon blocks on a Reichert OMU4 microtome using glass and diamond knives to a thickness of about 70 nm. The sections will be picked up on copper grids, stained with uranyl acetate and lead citrate for electron microscopy and examined on a JEOL 100 microscope. During electron microscopy, a systematic series of micrographs of endometrial cells will be taken at an initial magnification of X2000. The following sampling strategy will be used: 10 fields of view from each of six micrographs per block (two blocks per individual), giving 120 fields for each of the subjects. Measurements will be performed at X52000 and all magnifications will be determined using a grating replica with 2160 squares per mm. The volume fraction (Vv) of the nucleolus or NCS to the nucleus and the Vv of tubular components to the total channel system will be obtained by point counting as described in Williams (6 Practical Methods for Biological Microscopy 5-84 (1977)) which is incorporated herein for its description of point counting and related techniques. The results of this study will demonstrate no statistically significant effects of long-term mifepristone treatment on endometrial thickening at any time point.

Example 8

Intermittent Mifepristone Therapy vs. Myomectomy as Long-Term Treatments for Symptomatic Uterine Leiomyomata A study evaluating the effectiveness of intermittent mifepristone therapy (2.5 mg) against the effectiveness of myomectomy as a treatment for symptomatic uterine leiomyomata will be undertaken. The methods described in Example 1 will be used to recruit and enroll about 100 subjects into the study. 50 of the 100 subjects will be given intermittent daily mifepristone (2.5 mg) meaning that subjects will alternate between six months of daily mifepristone (2.5 mg) and 2 months of no treatment for four years. The remaining 50 subjects will undergo myomectomy at the beginning of the study.

During the four years of this study, measurements will be taken every six months. The measurements will mirror those described in Example 1 in all material regards. The results of the study will show that both groups of subjects show, on average, a decrease in blood loss, uterine volume and uterine leiomyomata size, improvements in Quality of Life Scores, and improvements in other symptoms including without limitation, a decrease in the occurrence and/or severity of pelvic pain, a decrease in the occurrence and/or severity of lower back pain, a decrease in the occurrence and/or severity of rectal pain, a decrease in the occurrence and/or severity of pelvic pressure, a decrease in the occurrence and/or severity of bladder pressure and a decrease in urinary frequency when compared to baseline measures. These results will demonstrate that intermittent mifepristone therapy provides a treatment option that is not significantly statistically different at the measures and time points taken from myomectomy, a far more invasive procedure and treatment.

Example 9

Mifepristone for Prevention of Breakthrough Bleeding in New Starters of Depo-medroxyprogesterone Acetate (DMPA)

The following study was conducted to primarily determine if mifepristone lowers the incidence of abnormal breakthrough uterine bleeding in new starters of the progestin contraceptive injection depo-medroxyprogesterone acetate (DMPA). The study also will test the effect of mifepristone on the contraceptive ability of DMPA to prevent ovulation in new starters of DMPA, will test the effect of mifepristone on estradiol and progesterone receptor concentrations in the endometrium of new starters of DMPA, and will test the effect of mifepristone on the function of estrogen receptors in the endometrium of new starters of DMPA.

DMPA is an effective, widely used progestin-only contraceptive injection that is administered about every 3 months. Unfortunately discontinuation rates as high as 40% have been reported during the first year of use due to the occurrence of breakthrough bleeding. Toppozada et al. 28 Contraception 1-20 (1983). The number of days of vaginal bleeding between the first and second injection can be around 30% of days and 20% of days between the second and third injection. Tyler et al., 21 Fertil. Steril. 469 (1970). Further, irregular or prolonged bleeding has been reported in 90% of subjects during the first 3 months of DMPA versus 34% during the 9-12th month of use. Newton et al. 14 (suppl 1) J. Obstet. Gynaecol.

1-34 (1994). Premature discontinuation of DMPA due to these problems can lead to unintended pregnancies and increased public health costs.

DMPA acts by suppressing gonadotropin production at the hypothalamic pituitary level and reliably blocks the midcycle LH surge, thus preventing ovulation. Clark et al. 75 Fertil. Steril. 871(2001). Estrogen and progesterone receptors change during the menstrual cycle, and estrogen and progesterone receptor isoforms have different effects on sex steroid responsive genes depending on the molecular context. Elger et al., 65 Steroids 713-723 (2000). Progestin-only contraceptives effect the expression of progesterone receptors depending on which specific receptor isoform was bound. Progestin-only contraceptives and mifepristone effect the expression of estrogen receptors. In one study, women on Norplant demonstrated increased endometrial estrogen receptor concentration, decreased endometrial progesterone receptor concentration and decreased breakthrough bleeding when administered mifepristone orally. Cheng et al., 15 Hum. Reprod. 1969 (2000).

The effect of mifepristone on endometrial estrogen and progesterone receptors has not been examined in women using DMPA, the most common progestin-only contraceptive in the United States. If mifepristone is demonstrated to decrease breakthrough bleeding in new starters of DMPA, it may encourage more women to maintain DMPA use during the first 6 months when breakthrough bleeding is at a maximum and therefore reduce the number of unintended pregnancies. Therefore, a study was conducted to gather data on the effect of mifepristone on breakthrough bleeding in new starters of DMPA.

Subjects: Subjects were recruited from patients presenting for routine gynecological care. Inclusion criteria for the study included that subjects be (i) female; (ii) 18-45 years; (iii) have a history of regular menstrual cycles (cycle length 21-35 days); (iv) agree to exclusively use non-hormonal methods of contraception such as barrier methods or sterilization (tubal sterilization or vasectomy) for the duration of the study; and (v) provide written, informed consent to participate in the study.

Exclusion criteria for the study included: (i) concomitant use of aminoglutethimide, carbamazepine, rifampicin, griseofulvin, barbiturates, phenytoin sodium, systemically administered steroids and thyroid hormones; (ii) undiagnosed abnormal genital bleeding; (iii) any epithelial cell abnormality as reported in the Bethesda System except reactive reparative changes with atypical squamous cells of undetermined significance (ASCUS); (iv) a well-documented history of a thrombotic event including stroke or, venous thromboembolism (deep venous thrombosis or pulmonary embolus). A history of superficial thrombophlebitis was not an exclusion criterion; (v) existing thromboembolic, cardiovascular or cerebrovascular disorder; (vi) cholestatic jaundice of pregnancy or past history of jaundice with prior us of hormonal contraception; (vii) current confirmed hypertension: defined as systolic >160 mmHG or diastolic >90 mmHG. Normal blood pressure on anti-hypertensive medication for previous 6 months was allowed; (viii) DMPA injection within the prior 6 months; (ix) oral contraceptive use within the past 3 months; (x) contraceptive implants within the past 6 months; (xi) IUD use within the past 3 months; (xii) heavy smoking (>10 cigarettes per day); (xiii) active or history of hepatic or renal disease. Hepatic disease is defined as having an AST/SGOT and/or ALT/SGPT 2.5 times upper limit of normal and/or total bilirubin >2.0 mg/dL; renal disease is defined as having a creatinine >1.8 mg/dL; (xiv) insulin dependent diabetes mellitus or non-insulin dependent diabetes mellitus that is poorly controlled; (xv) hypersensitivity to study medications; (xvi) concurrent use of other investigational medications; (xvii) significant anemia (hemoglobin <10.8 mg/dL); and (xviii) women who are post-partum or post-abortion who have not had at least 2 regular periods.

After obtaining informed consent, study candidates underwent a screening examination and laboratory tests similar to those described in Example 1. Those who passed the initial screening tests underwent a baseline month in which one biopsy was performed and urine collected to measure metabolites of progesterone in order to create ovulatory reference ranges. Subjects who were found to be ovulatory based on serum progesterone and who tolerated the endometrial biopsies were randomized to study medication. Subjects will receive a total of 4 injections of DMPA (intramuscularly once every 3 months) and return to the clinic every 14 days for twelve 28-day cycles to receive a dose of mifepristone or placebo. Subjects will undergo 3 additional biopsies over 12 cycles. Cervical mucus scores will be determined at the time of each biopsy. Subjects will record daily bleeding, medications and side effect information on diaries for the duration of the study. Blood will be drawn weekly for measurement of serum progesterone after the initial dose of DMPA. These measurements will be done on a batched basis. The entire study will require 50 scheduled visits and the subjects will be compensated as follows: reimbursement for time, travel and out of pocket expenses at a rate of $25 for each of 44 brief visits, $50 for the initial and exit visit and $75 for each of 4 biopsy visits for a total of $1500 for the 13 month study.

Endometrial biopsies will be analyzed using PCR and immunohistochemistry to determine concentrations of estrogen and progesterone receptor isoforms. A portion of the biopsy material will be reserved for cell culture in order to determine proliferation assays as a marker of estrogen receptor function.

The primary endpoint of the study will be the number of days of breakthrough bleeding during the first 6 months of DMPA. Thus a 2-sided, 0.05-level, two-sided t-test will be used to compare the group of subjects receiving mifepristone to those receiving placebo. With 25 subjects in each of the two arms, there will be 93% power to observe a statistically significant difference between the two groups using a 2-sided, 0.05 level two-sample t-test.

Mifepristone was provided by Danco Laboratories. Danco Laboratories provided the pure mifepristone powder for the study. Mifepristone capsules were prepared by a member of the hospital pharmacy staff by weighing 50 mg of pure powder and packing it into empty opaque gel capsules. Placebo capsules contain powdered sugar. An amount that approximates the volume occupied-by 50 mg of mifepristone powder is packed into opaque gel capsules by a member of the hospital pharmacy staff.

To date, the results show that based on 1148 and 1232 women-days of observation in the placebo and mifepristone groups respectively, median percentage days of bleeding was 30% and 11% (p<0.05). Further, no adverse events have occurred to date. Thus, this study has demonstrated the effectiveness of mifepristone as a treatment to inhibit breakthrough bleeding otherwise caused by DMPA. Other measures and results collection are on-going.

Example 10

Low Dose Mifepristone Administered After Birth Control Pills

Birth control pills can be used as a treatment for severe dysmenorrhea, polymenorrhea and dysfunctional uterine bleeding (DUB). While birth control pills can be effective at reducing the symptoms associated with these conditions, they are not effective in some subjects. The following study will be conducted to confirm that a low dose of mifepristone can be effective to reduce the symptoms associated with these conditions when treatment with birth control pills has failed to provide adequate relief.

Subjects: Subjects with severe dysmenorrhea, polymenorrhea or DUB will be recruited through direct advertising and physician referrals. A total of 240 subjects will be included in the study. Eighty subjects will have severe dysmenorrhea, eighty subjects will have polymenorrhea and eighty subjects will have DUB. All subjects will have undergone previous treatment for their respective condition with the use of birth control pills, the birth control pills providing inadequate relief of symptoms. At the time of entering the study, subjects will have stopped taking birth control pills as a treatment for their symptoms within the previous about 30 days. Of the eighty subjects with each condition, twenty will receive placebo, twenty will receive 1.0 mg mifepristone, twenty will receive 2.5 mg mifepristone and twenty will receive 5.0 mg mifepristone manufactured and treated as described in Example 1. No other medications will be taken by the subjects during the assessment period.

For polymenorrhea and DUB subjects, severity of vaginal bleeding will be assessed by the subjects each day throughout the course of the study using a pictorial chart. As stated earlier, this assessment of menstrual bleeding has been previously validated. Janssen et al., 85 Obstet. Gynecol. 977-82 (1995); Higham et al., 97 Br. J. Obstet. Gynecol. 734-39 (1990). For severe dysmenorrhea subjects, severity of disability will be self-evaluated both just before the onset of and during menstruation using a 6-point scale (0: no disability; 1: mild disability; 2: moderate disability; 3: strong disability; 4: severe disability; 5: no activity possible) three times a day. All subjects will also rate the occurrence or severity of any unpleasant effects of mifepristone administration daily throughout the course of the study using a 4-point scale (0: no unpleasant effects; 1: mildly unpleasant effects; 2: moderately unpleasant effects; 3: strongly unpleasant effects). The study will be conducted over about a six month period. For inclusion in the severe dysmenorrhea portion of the study, a patient must have self-evaluated with a score of three or above for at least two menstrual cycles before entering the study.

The study demonstrates the usefulness of low doses of mifepristone, including 1.0 mg, 2.5 mg and 5.0 mg in reducing the symptoms associated with severe dysmenorrhea, polymenorrhea or DUB after treatment with birth control pills has failed to adequately treat the symptoms of these conditions. Regarding potential adverse effects of these doses of mifepristone, there are no significant differences between the groups receiving any of the doses of mifepristone as compared to placebo. Thus, this study demonstrates that the administration of low doses of mifepristone are effective at reducing the occurrence or severity of symptoms associated with severe dysmenorrhea, polymenorrhea or DUB and is also well-tolerated by subjects at the test doses.

These data demonstrate that the present invention provides low dosage anti-progestational agent treatment and/or treatment with an anti-progestational agent for a shorter period of time than previously known in the art.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention. Moreover, any one or more features of any embodiment of the invention can be combined with any one or more other features of any other embodiment of the invention, without departing from the scope of the invention.

Example 11

5 mg Daily Mifepristone for the Treatment of Symptomatic Uterine Leiomyomata

A randomized, double-blinded, placebo-controlled study was carried out on the effectiveness of mifepristone, 5 mg daily for 6 months, for treating uterine leiomyomata and its related symptoms, including quality of life, bleeding, uterine and leiomyoma size, and pain. The Study and Results are described in Fiscella et al., Obstetrics & Gynecology, 108(6) (2006), hereby incorporated by reference in its entirety. Eligible Study Subjects included premenopausal women 18 years of age or older who reported at least moderately severe leiomyoma-related symptoms (more than 39 on the Uterine Fibroid Symptom Quality of Life Symptom Severity Subscale), had a total uterine volume by vaginal and abdominal ultrasound 160 mL or more and at least one leiomyoma that was 2.5 cm or larger, had not used short-acting hormones in the past 3 months, and had not used gonadotropin-releasing hormone analogues or other long-acting hormonal medications in the past 6 months. Women were excluded if they were pregnant or intended to become pregnant during the next 6 months or had major medical morbidity or severe anemia, active mental illness, elevated liver enzymes, or substance abuse. Participants agreed to use barrier contraception and not to use hormonal or surgical treatments for leiomyomata during the course of the trial. Analgesic use was permitted.

Using design 42 Study Subjects were randomly assigned to take either 5 mg mifepristone daily or a placebo, with twenty-two were randomized to treatment and 20 to placebo. Outcomes were assessed using mean change in leiomyoma-specific overall quality of life (Uterine Fibroid Symptom Quality of Life) scale 1-100 as the primary outcome, which includes secondary scales to measure perceived impact of leiomyomata on activities of daily living, general concern and worry, energy and mood, sense of self-control, self-consciousness, and sexual functioning. Secondary measures included global health status (Medical Outcomes 36-item Short Form [SF-36] survey) and global pain (McGill Pain Questionnaire). Each questionnaire was administered at baseline, 1 month, 3 months, and 6 months, except the McGill Pain Questionnaire, which was assessed monthly. Bleeding was assessed by using daily menstrual logs and pictorial bleeding charts. A monthly blood loss index was calculated from menstrual history by assigning values 1-4 to each day of spotting, indicating light, moderate, and heavy flow, respectively, and then summing the results. Monthly assessments of the presence and intensity of likely leiomyoma symptoms (including pelvic pain, pelvic pressure, bladder pressure, urinary frequency, low back pain, rectal pain, and pain with intercourse) and drug adverse effects (including hot flushes, headache, nausea, vomiting, mood swings, diarrhea, decreased libido, weakness, fatigue, and nervousness) were performed with a standardized instrument consisting of 5-point Likert scale items. Uterine volume and leiomyoma size and number were assessed by vaginal and/or abdominal ultrasonogram (depending on leiomyoma size) at baseline, 1 month, 3 months, and 6 months. The uterus was measured in three planes and a total volume calculated. The five largest leiomyomata were identified, a volume calculated for each of the leiomyomata, and the results summed.

Baseline uterine volume was subtracted from each subsequently measured uterine volume, and volume changes were analyzed.

The final analysis was powered to detect a 25-point difference in mean Uterine Fibroid Symptom Quality of Life scores. Differences in Uterine Fibroid Symptom Quality of Life scores, ultrasound measures, bleeding, pain, and other longitudinal measures were assessed by using individual growth curve models. Independent variables included in each model were treatment group, month, and an interaction term for treatment group and month (used to assess whether the treatment effect of mifepristone changed with time). Approximate t tests were used to test hypotheses of between-group and within-group differences in outcomes.

Mean Uterine Fibroid Symptoms Quality of Life leiomyoma-specific quality of life measures were similar between groups at baseline. Significant improvements were seen in the treatment group compared with the placebo group for leiomyoma-specific quality of life (P<0.001; FIG. 2) and aspects including concern (P<0.001), activities (P<0.001), energy and mood (P=0.009), control (P=0.02), self-consciousness (P=0.008), and sexual functioning (P=0.03). By 6 months, mean Uterine Fibroid Symptoms Quality of Life measures increased by an average of 50.1 of a possible 100 points (range 0-86), or 135%, and by 16.7 points (range 14-73) among placebo controls, or a 41%. Symptom severity decreased significantly in both the treatment and placebo groups, but the 6-month scores showed a significantly greater decline among women receiving the treatment (67 to 21) than among women receiving placebo (67 to 50).

Figure 3:
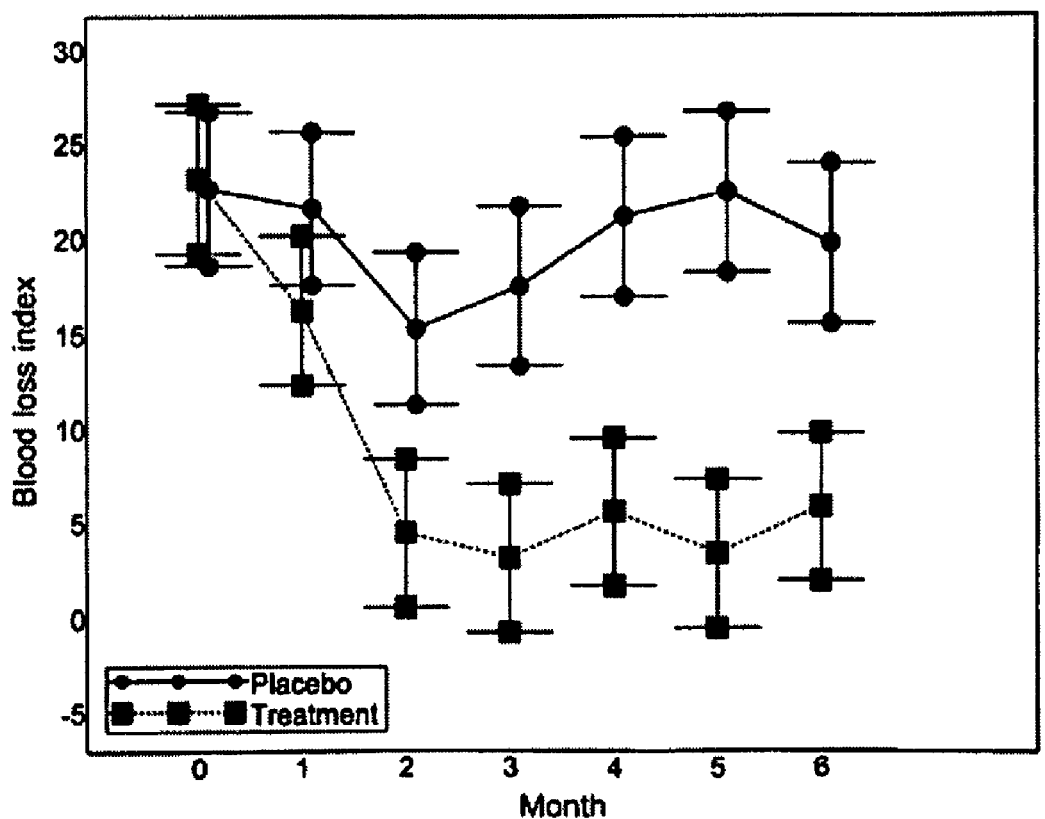
FIG. 3 is a graph showing the change in bleeding patterns as a function of treatment duration among mifepristone and placebo groups. Bleeding patterns were measured by bleeding scores derived from product of bleeding intensity from pictorial blood chart and days of bleeding. Bars refer to 95% confidence intervals surrounding changes in bleeding patterns at each time point.

Treatment with mifepristone was also associated with improvements in energy and fatigue, health status change, and pain based on SF-36 subscales, but not for physical functioning, physical health, emotional health, emotional well-being, social functioning, or general health. Bleeding decreased markedly among women in the treatment group but not in the placebo group. By the sixth month, 9 of 22 (41%) women in the treatment group had become amenorrheic, compared with none of the women in the placebo group. Mean blood loss index values were significantly lower in the treatment group (P<0.001; FIG. 3). Treatment had a significant effect on mean hemoglobin levels (P<0.001); mean hemoglobin levels increased in the treatment group from 12.0 to 13.5 g/dL (P<0.001) and decreased in the placebo group from 12.2 to 11.6 g/dL (P=0.11). Anemia, defined as hemoglobin levels below 12.0 g/dL, was present in 11 of 22 (50%) women in the treatment group and in 9 of 20 (45%) women in the placebo group at baseline (Fisher exact test; P>0.05). After six months of treatment, 2 of 22 (9%) women in the treatment group and 12 of 20 (60%) women in the control group were anemic (Fisher exact test; P<0.001).

Figure 4:
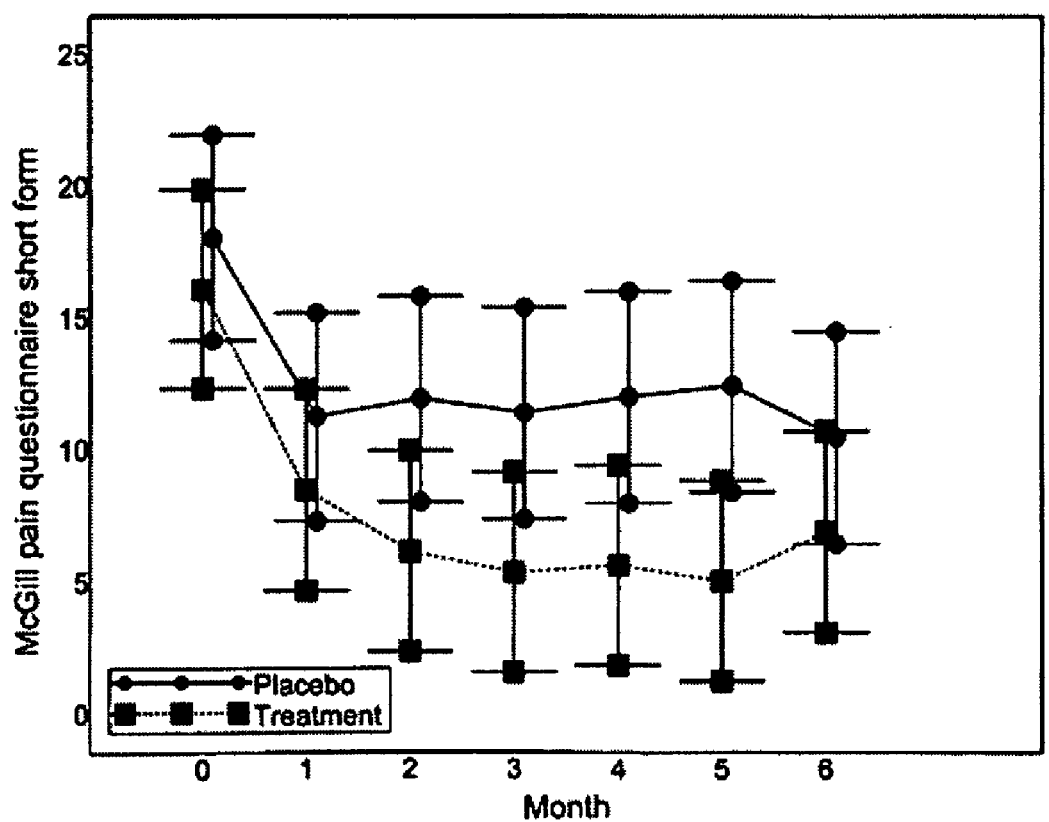
FIG. 4 is a graph showing the change in pain, measured using the McGill Pain Questionnaire (Short Form), as a function of treatment duration among mifepristone and placebo groups. Bars refer to 95% confidence intervals surrounding change in the score at each time point.

The treatment group reported decreases in pain as measured by the McGill Pain Questionnaire (FIG. 4), but group differences compared with the placebo group did not reach statistical significance.

Figure 5:
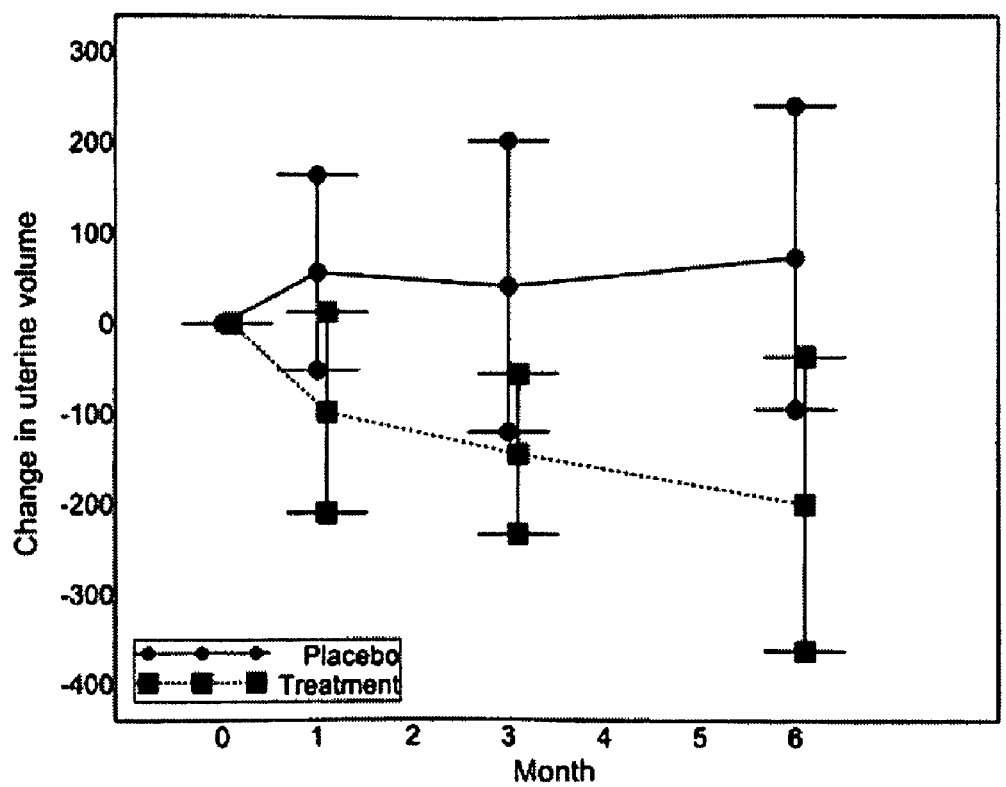
FIG. 5 is a graph showing the change in uterine volumes (mL), measured by vaginal and abdominal ultrasonography, as a function of treatment duration among mifepristone and placebo groups. Bars refer to 95% confidence intervals surrounding changes in uterine volume at each time point.

Uterine volume (FIG. 5) decreased an average of 200 mL among treatment group women (P=0.02) and increased an average of 73 mL in the placebo group (P=0.37). The effect of treatment on mean uterine volume was highly significant (P<0.001). A secondary regression of uterine volume adjusted for individual baseline volume indicated that uterine volumes decreased an average of 47% in the treatment group and increased an average 10% in the placebo group. Similar and statistically significant differences in reduction in leiomyoma size were noted between groups.

Monthly reports of symptoms including pelvic pain, pelvic pressure, bladder pressure, urinary frequency, low back pain, rectal pain, and pain with intercourse all showed improvements in the treatment group, but not in the placebo group. However, group differences were statistically significant only for pain with intercourse (P<0.05) and marginally significant for pelvic pressure (P=0.06).

Potential medication adverse effects were uncommon in both groups. Neither the incidence nor severity of adverse effects, including headache, nausea, vomiting, mood swings, diarrhea, decreased libido, weakness, fatigue, hot flushes, and nervousness, statistically differed between the two groups. Rates of women were higher among the placebo group (P<0.01). None of the participants showed abnormal liver function during the study. Analgesic use did not differ between groups. No endometrial hyperplasia or other significant endometrial pathology was observed during the study. Higher rates of a characteristic pattern of cystic glandular dilatation were noted among the endometria of treated women.

At the end of the study, 19 of 20 (95%) women in the treatment group correctly guessed that they had been receiving mifepristone. The remaining woman said she was unsure. Of the 17 women in the placebo group who finished the trial, 9 (53%) correctly guessed they were not receiving the drug, 4 (24%) guessed that they had been receiving the drug, and 4 (24%) said they were unsure. The difference between these two groups in correct guesses is significant (Fisher exact test; P=0.007).

Thus, treatment with mifepristone 5 mg daily for 26 weeks substantially improved leiomyoma-specific related quality of life and bleeding and reduces uterine volume and leiomyoma size among women with symptomatic leiomyomata. Most of the improvement in symptoms and quality of life occurred during the first 8-12 weeks of treatment although reduction in uterine and leiomyoma volume continued to 6 months. Comparable benefits were seen in African-American and white women although power to detect differences by subgroup was limited. Notably, the magnitude of improvement in quality of life (using the same measure) was comparable with that reported in observational studies of uterine artery embolization. No improvements were noted using global measures of pain (McGill Pain Questionnaire) or global physical or mental health status (SF-36) suggesting that benefits of the drug were confined primarily to leiomyoma-specific symptoms.

The drug was well tolerated, as evidenced by low dropout rate and absence of appreciable difference in adverse effects between treatment and control groups. No case of endometrial hyperplasia was noted in this study.

What is claimed is:

1. A method of treatment comprising administering an anti-progestational agent to a patient in an amount of about 3.75 mg or less to treat uterine leiomyomata, wherein the anti-progestational agent is mifepristone.

2. The method of claim 1, wherein said anti-progestational is administered to the patient for less than one month.

3. The method of claim 1, wherein said amount is about 2.5 mg or less.

4. The method of claim 1, wherein said amount is about 1.25 mg or less.

5. The method of claim 1, wherein said anti-progestational agent is administered after the conclusion of treatment with a GnRh analogue.

6. The method of claim 1, wherein said anti-progestational agent is administered after the conclusion of a treatment selected from the group consisting of myomectomy, uterine artery embolization, and ultrasound therapy.

7. The method of claim 1, wherein said anti-progestational agent is administered prior to a surgical treatment.

8. The method of claim 7, wherein said surgical treatment is selected from the group consisting of hysterectomy, myomectomy, uterine artery embolization and endometrial ablation.

9. The method of claim 1, wherein said anti-progestational agent is administered prior to labor and delivery.

10. The method of claim 1, wherein said anti-progestational agent is administered daily.

11. The method of claim 1, wherein said anti-progestational agent is administered by a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

12. The method of claim 1, wherein said anti-progestational agent is administered in a dosage form selected from the group consisting of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray.

13. The method of claim 12, wherein said dosage form is a sustained release dosage form.

14. The method of claim 1, wherein said patient is a pre-menopausal female over the age of 18.

15. The method of claim 1, wherein said patient has at least one uterine leiomyomata that is $\geq 2.5$ cm in size.

16. The method of claim 1, wherein said patient has a total uterine volume of 160 cc.

17. The method of claim 1, further comprising administering a maintenance dose of said anti-progestational agent to said patient in an amount of about 2.5 mg or less after administering said anti-progestational agent in an amount of about 3.75 mg or less.

18. The method of claim 17, wherein said maintenance dose is in an amount less than or equal to 50% of said amount of about 3.75 mg or less.

19. The method of claim 17, wherein said anti-progestational agent in an amount of about 3.75 mg or less is administered for less than one month.

20. A dosing regimen comprising directing an anti-progestational agent to be administered to a patient in an amount of about 3.75 mg or less per day to treat uterine leiomyomata, wherein the anti-progestational agent is mifepristone.

21. The dosing regimen of claim 20, wherein said anti-progestational agent is directed to be administered for less than one month.

22. The dosing regimen of claim 20, wherein said anti-progestational agent is directed to be administered in an amount of about 2.5 mg or less.

23. The dosing regimen of claim 20, wherein said anti-progestational agent is directed to be administered in an amount of about 1.25 mg or less.

24. The dosing regimen of claim 20, wherein said anti-progestational agent is directed to be administered after the conclusion of treatment with a GnRh analogue.

25. The dosing regimen of claim 20, wherein said anti-progestational agent is directed to be administered after the conclusion of a treatment selected from the group consisting of myomectomy, uterine artery embolization, and ultrasound therapy.

26. The dosing regimen of claim 20, wherein said anti-progestational agent is directed to be administered prior to a surgical treatment.

27. The dosing regimen of claim 20, wherein said anti-progestational agent is directed to be administered to shrink uterine leiomyomata before a surgical treatment.

28. The dosing regimen of claim 27 wherein said surgical treatment is selected from the group consisting of hysterectomy, myomectomy, uterine artery embolization and endometrial ablation.

29. The dosing regimen of claim 20, wherein said anti-progestational agent is directed to be administered prior to labor and delivery.

30. The dosing regimen of claim 20, wherein said anti-progestational agent is directed to be administered daily.

31. The dosing regimen of claim 20, wherein said anti-progestational agent is directed to be administered intermittently.

32. The dosing regimen of claim 20, wherein said anti-progestational agent is directed to be administered by a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

33. The dosing regimen of claim 20, wherein said anti-progestational agent is directed to be administered in a dosage form selected from the group consisting of a tablet, a capsule, a cachet, a dragee, a pill, pellets, granules, a powder, a solution, an emulsion, a fluid emulsion, a suspension, a fluid suspension, a semi-solid, an ointment, a paste, a cream, a gel, a jelly, a foam, an implant, a patch and a spray.

34. The dosing regimen of claim 33, wherein said dosage form is a sustained release dosage form.

35. The dosing regimen of claim 20, wherein said patient is a pre-menopausal female over the age of 18.

36. The dosing regimen of claim 20, wherein said patient has at least one uterine leiomyomata that is 2.5 cm in size.

37. The dosing regimen of claim 20, wherein said patient has a total uterine volume of $\geq 160$ cc.

38. The dosing regimen of claim 20, further comprising directing a maintenance dose of said anti-progestational agent to be administered to said patient in an amount of about 2.5 mg or less after administering said anti-progestational agent in an amount of about 3.75 mg or less.

39. The dosing regimen of claim 38, wherein said maintenance dose is directed to be administered in an amount less than or equal to 50% of said amount of about 3.75 mg or less.

40. The method of claim 38, wherein said anti-progestational agent in an amount of about 3.75 mg or less is directed to be administered for less than one month.

41. A business method comprising the step of providing to a consumer an anti-progestational agent in equivalent dosage units of about 3.75 mg or less and a dosing regimen wherein said dosing regimen directs said anti-progestational agent to be administered to a patient to treat uterine leiomyomata, wherein said anti-progestational agent is mifepristone and wherein said dosing regimen directs said anti-progestational agent to be administered in an amount of about 3.75 mg or less per day.

42. The business method of claim 41, wherein said anti-progestational agent is provided in equivalent dosage units of about 2.5 mg or less, and said dosing regimen directs said anti-progestational agent to be administered in an amount of about 2.5 mg or less.

43. The business method of claim 41, wherein said anti-progestational agent is provided in equivalent dosage units of about 1.25 mg or less of said anti-progestational agent, and said dosing regimen directs said anti-progestational agent to be administered in an amount of about 1.25 mg or less per day.

44. The business method of claim 41, wherein said anti-progestational agent is provided in an amount of less than about 40 dosage units, and said dosing regimen directs said anti-progestational agent to be administered for less than one month.

45. The business method of claim 41, wherein said dosing regimen directs said anti-progestational agent to be administered to the patient as a maintenance dose in an amount of about 2.5 mg or less after administering said anti-progestational agent in an amount of about 3.75 mg or less.

46. The business method of claim 45, wherein said dosing regiment directs said anti-progestational agent in an amount of about 3.75 mg or less and said maintenance dose in an amount of about 2.5 or less to be administered daily.

47. The business method of claim 45, wherein said anti-progestational agent is provided as a first set of equivalent dosage units, each comprising about 3.75 mg or less of said anti-progestational agent, and a second set of equivalent dosage units, each comprising about 2.5 mg or less of said anti-progestational agent.

* * * * *

UNITED STATES PATENT AND TRADEMARK OFFICE
CERTIFICATE OF CORRECTION

| | | |
|---|---|---|
| PATENT NO. | : 8,173,626 B2 | Page 1 of 1 |
| APPLICATION NO. | : 11/715509 | |
| DATED | : May 8, 2012 | |
| INVENTOR(S) | : Richard Hausknecht | |

It is certified that error appears in the above-identified patent and that said Letters Patent is hereby corrected as shown below:

Claim 16, column 65, line 35:
"uterine volume of 160 cc" should read -- uterine volume of $\geq$ 160 cc --.

Claim 36, column 66, line 43:
"has at least one uterine leiomyomata that is 2.5 cm in size" should read -- has at least one uterine leiomyomata that is $\geq$ 2.5 cm in size --.

Signed and Sealed this
Twenty-sixth Day of June, 2012

David J. Kappos
*Director of the United States Patent and Trademark Office*